United States Patent [19]
Imai et al.

[11] Patent Number: 5,170,809
[45] Date of Patent: Dec. 15, 1992

[54] POWERED DENTAL FLOSS

[75] Inventors: Takahiro Imai, Habikino; Yoji Kawamoto, Hikone, both of Japan

[73] Assignee: Matsushita Electric Works, Ltd., Osaka, Japan

[21] Appl. No.: 807,590

[22] Filed: Dec. 16, 1991

[30] Foreign Application Priority Data

Dec. 25, 1990 [JP] Japan .................................. 2-406160
May 28, 1991 [JP] Japan .................................. 3-121615

[51] Int. Cl.⁵ ............................................. A61C 15/00
[52] U.S. Cl. .................................. 132/322; 132/323
[58] Field of Search ................................. 132/322, 323

[56] References Cited

U.S. PATENT DOCUMENTS

| | | | |
|---|---|---|---|
| 3,421,524 | 1/1969 | Waters | 132/322 |
| 3,667,483 | 6/1972 | McCabe | 132/322 |
| 3,759,274 | 9/1973 | Warner | 132/322 |
| 3,847,167 | 11/1974 | Brien | 132/322 |
| 4,014,354 | 3/1977 | Garrett | 132/322 |
| 4,235,253 | 11/1980 | Moore | 132/322 |
| 4,338,957 | 7/1982 | Meibauer | 132/322 |
| 4,830,032 | 5/1989 | Jousson | 132/323 |
| 4,880,382 | 11/1989 | Moret et al. | 433/118 |

FOREIGN PATENT DOCUMENTS

90/11057 10/1990 World Int. Prop. O. .......... 132/322

Primary Examiner—John J. Wilson
Attorney, Agent, or Firm—Stevens, Davis, Miller & Mosher

[57] ABSTRACT

A powered dental floss includes a floss and a hand grip provided with an output shaft which has a longitudinal axis and to which the floss is coupled. The hand grip incorporates a motor and a drive mechanism which is powered by the motor to impart a vibrating motion to the output shaft. The floss is stretched substantially in parallel with the longitudinal axis of the output shaft so that it is driven to vibrate along its length for effectively cleaning between the teeth.

16 Claims, 24 Drawing Sheets

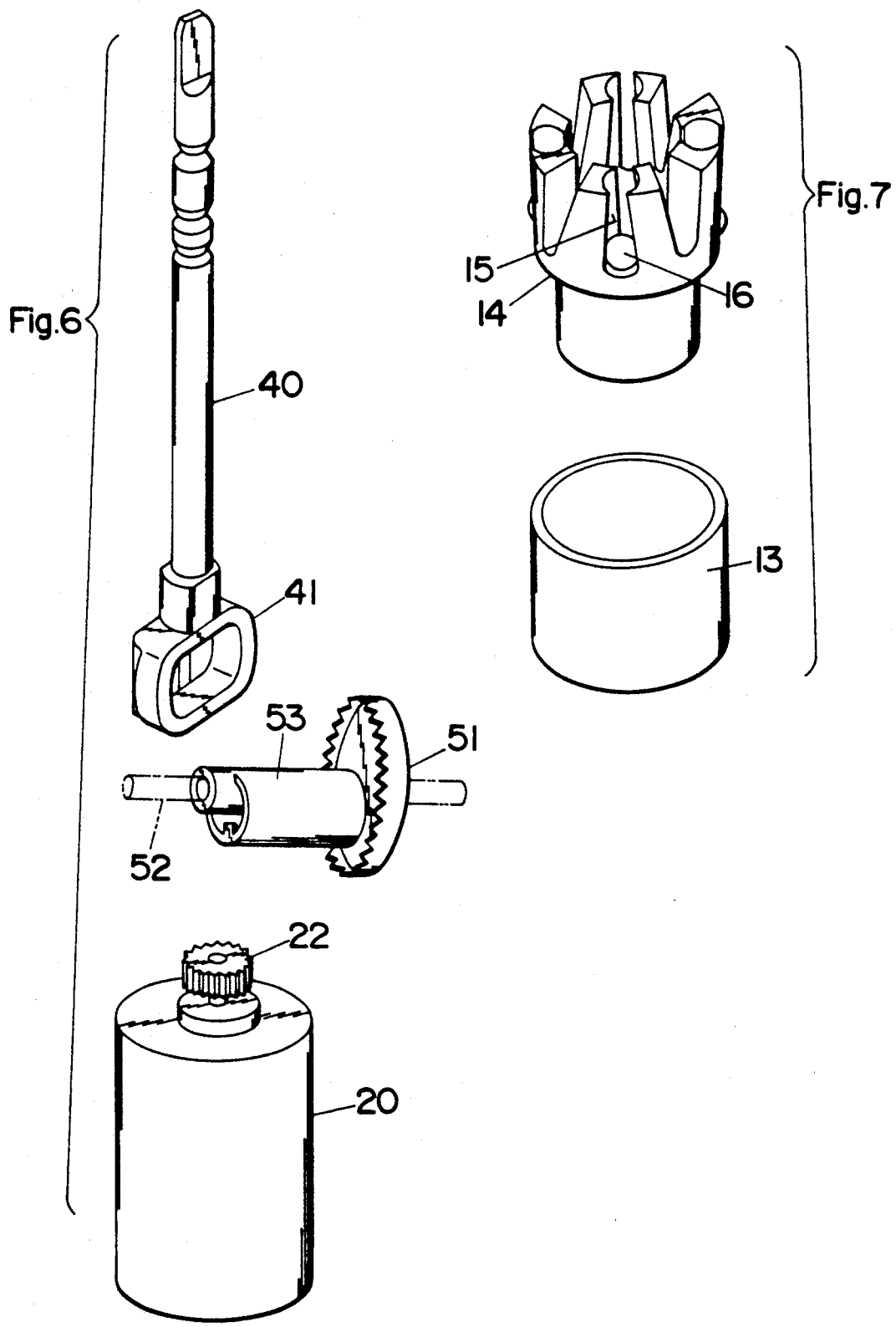

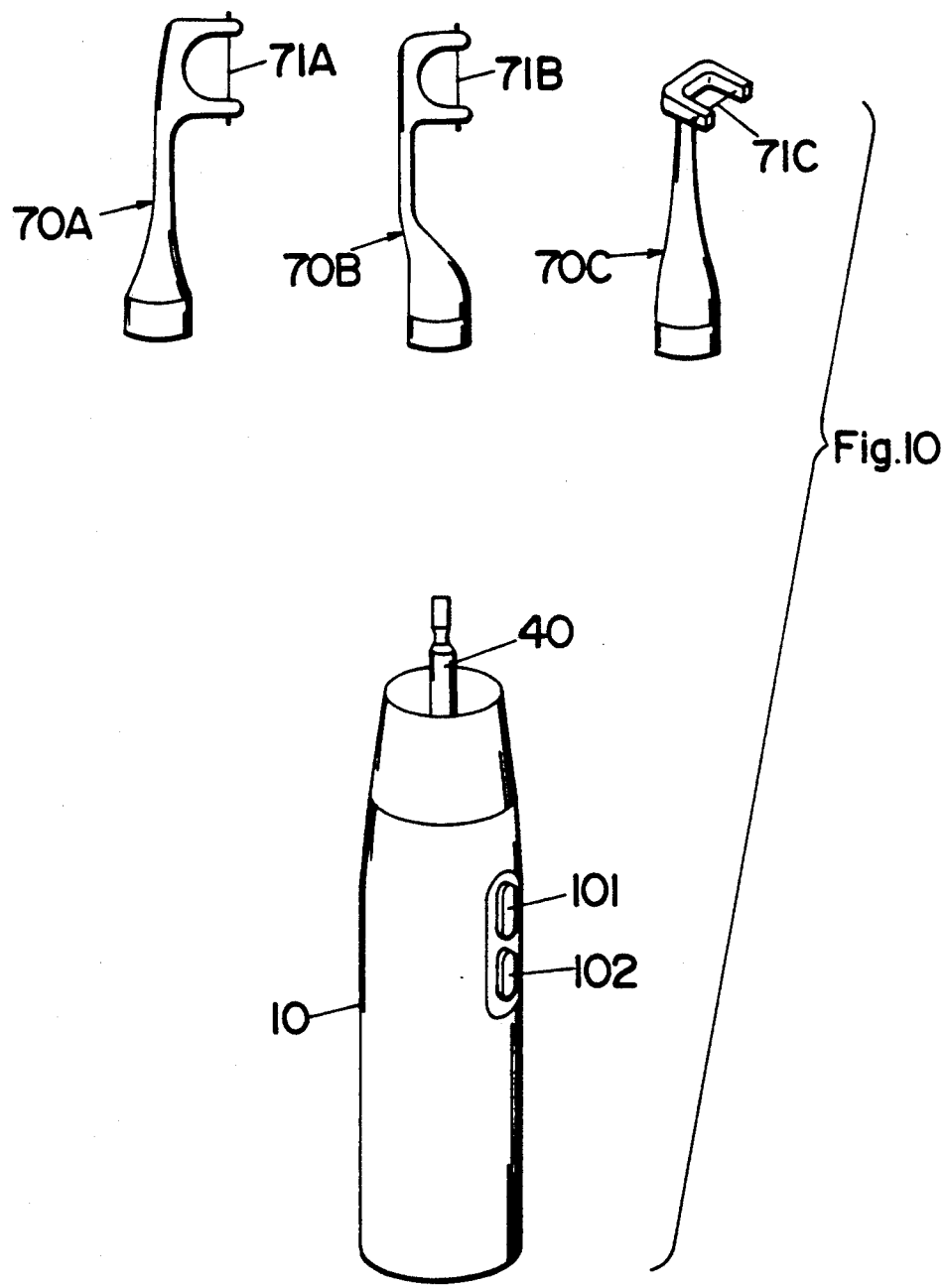

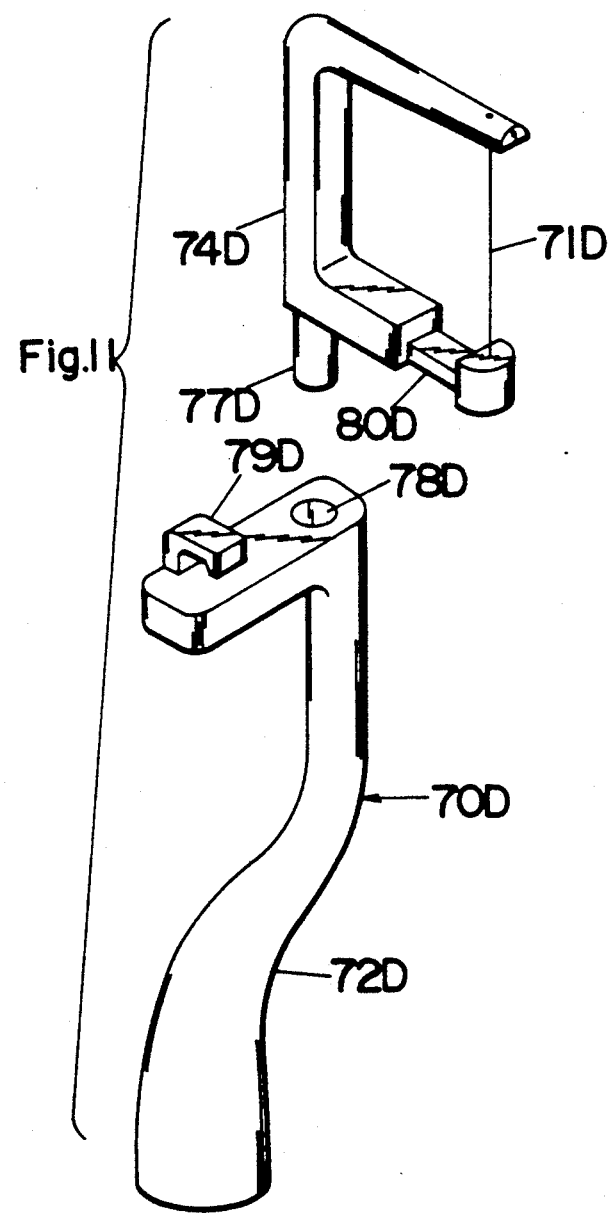

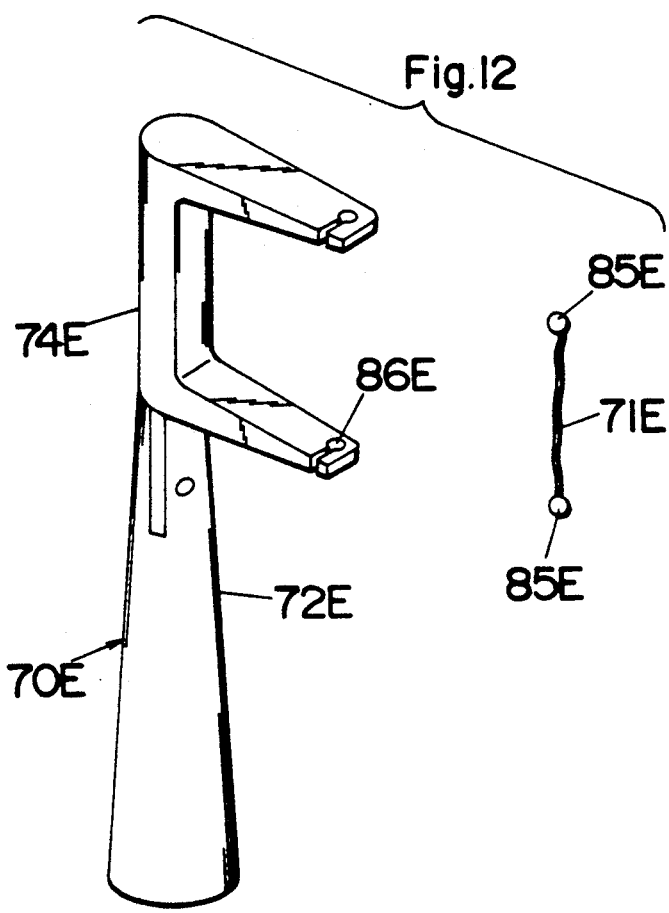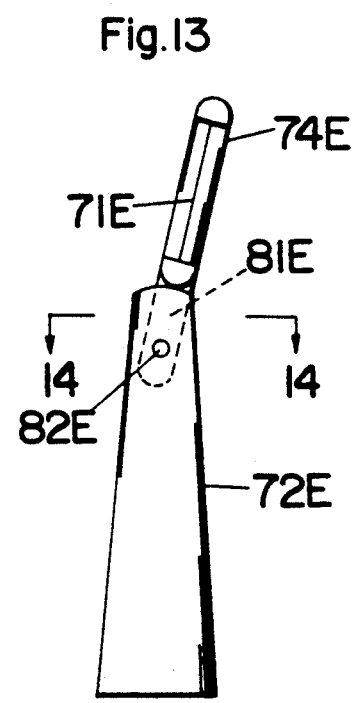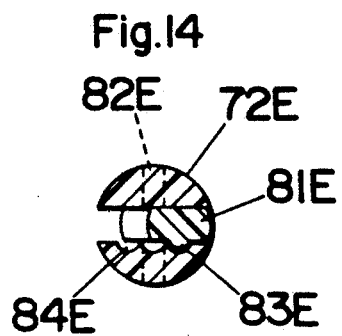

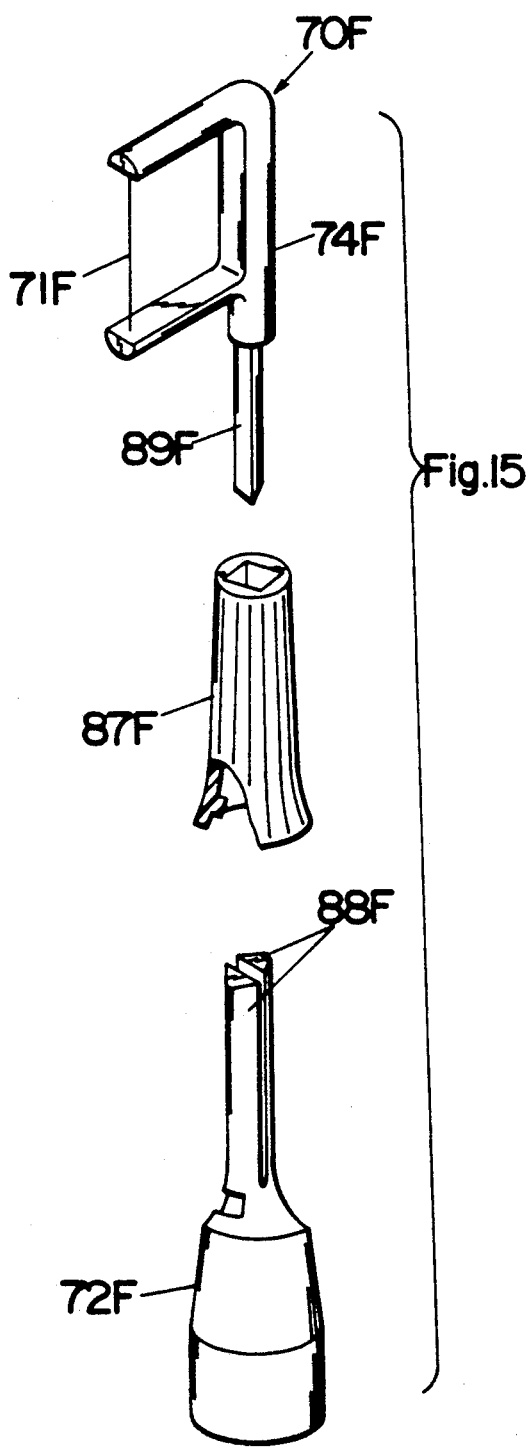

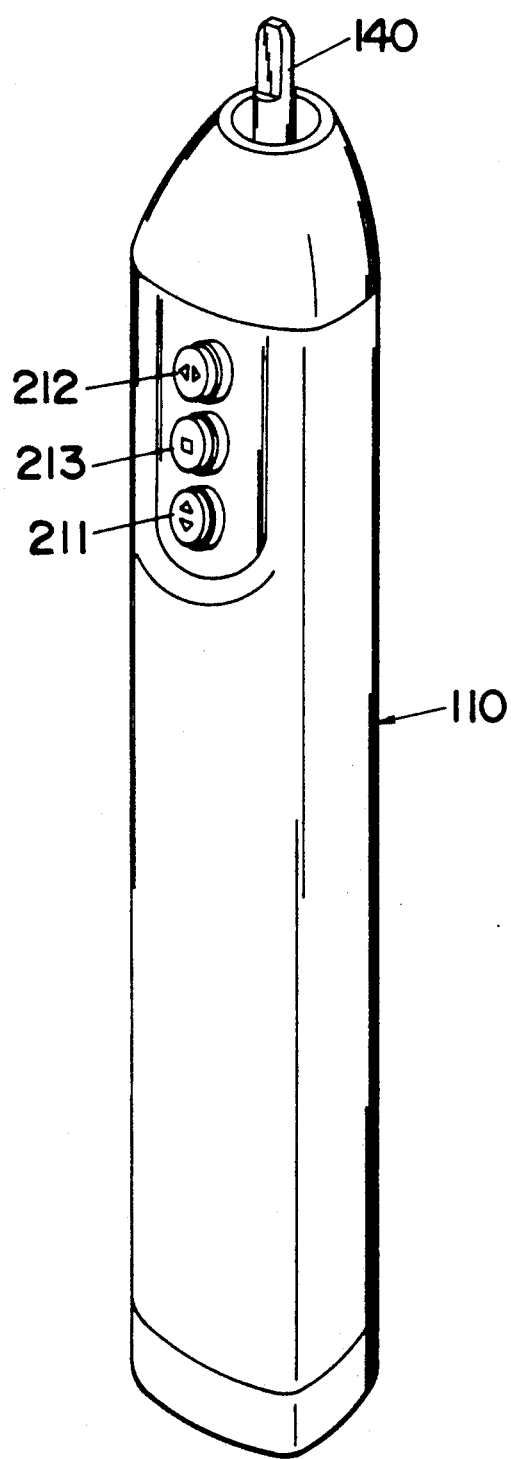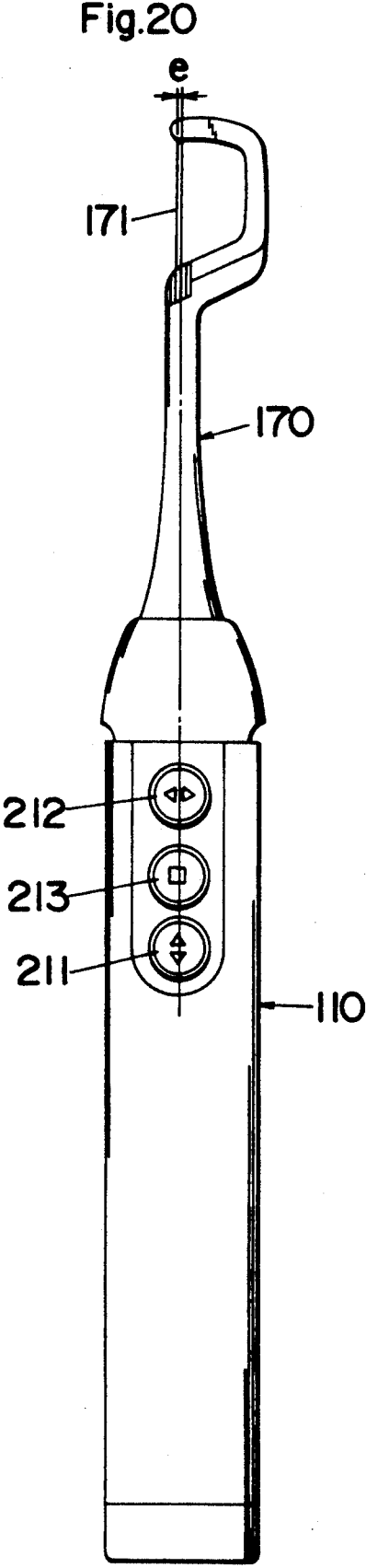

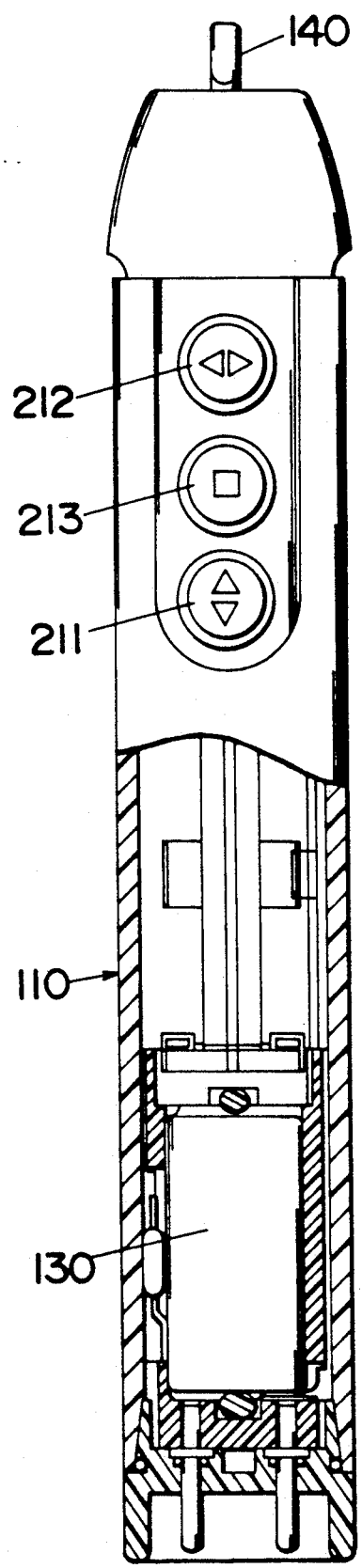
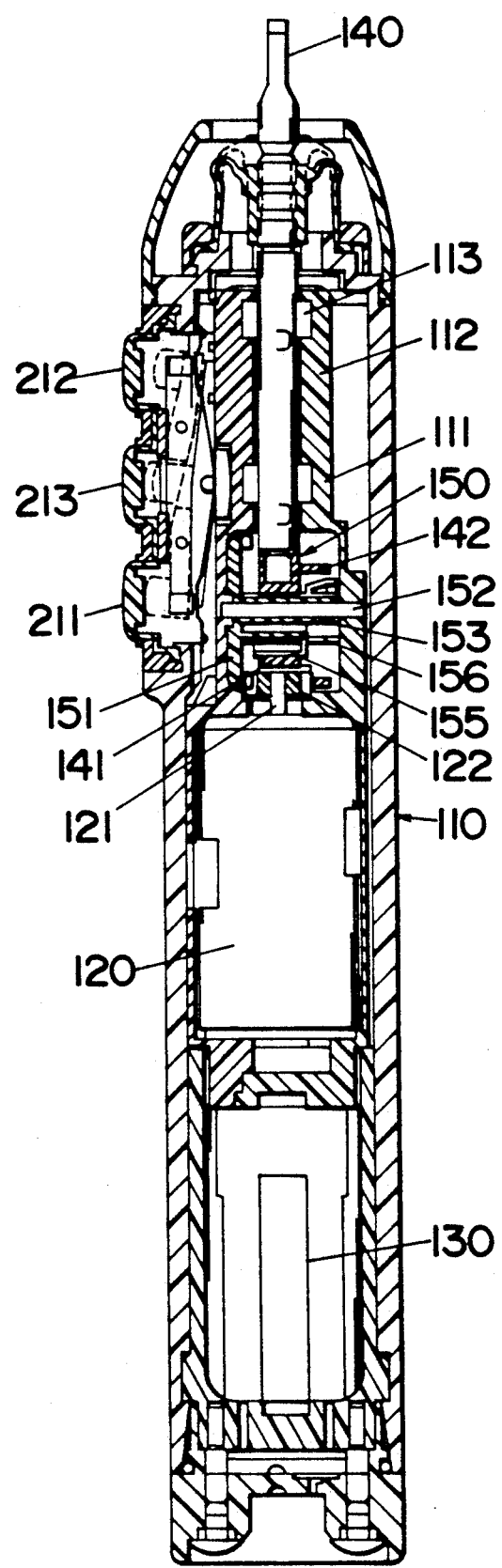
Fig.22
Fig.23

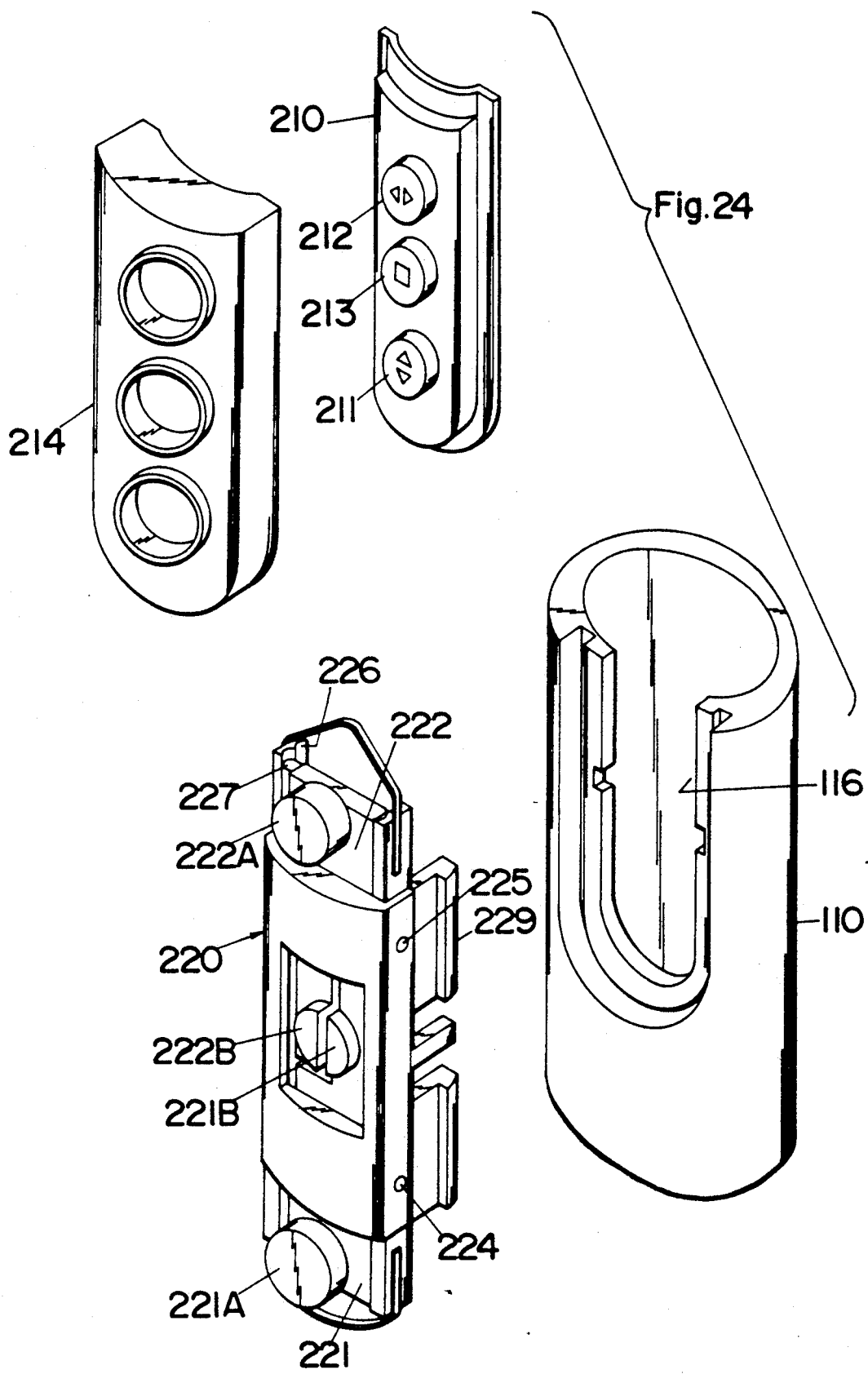

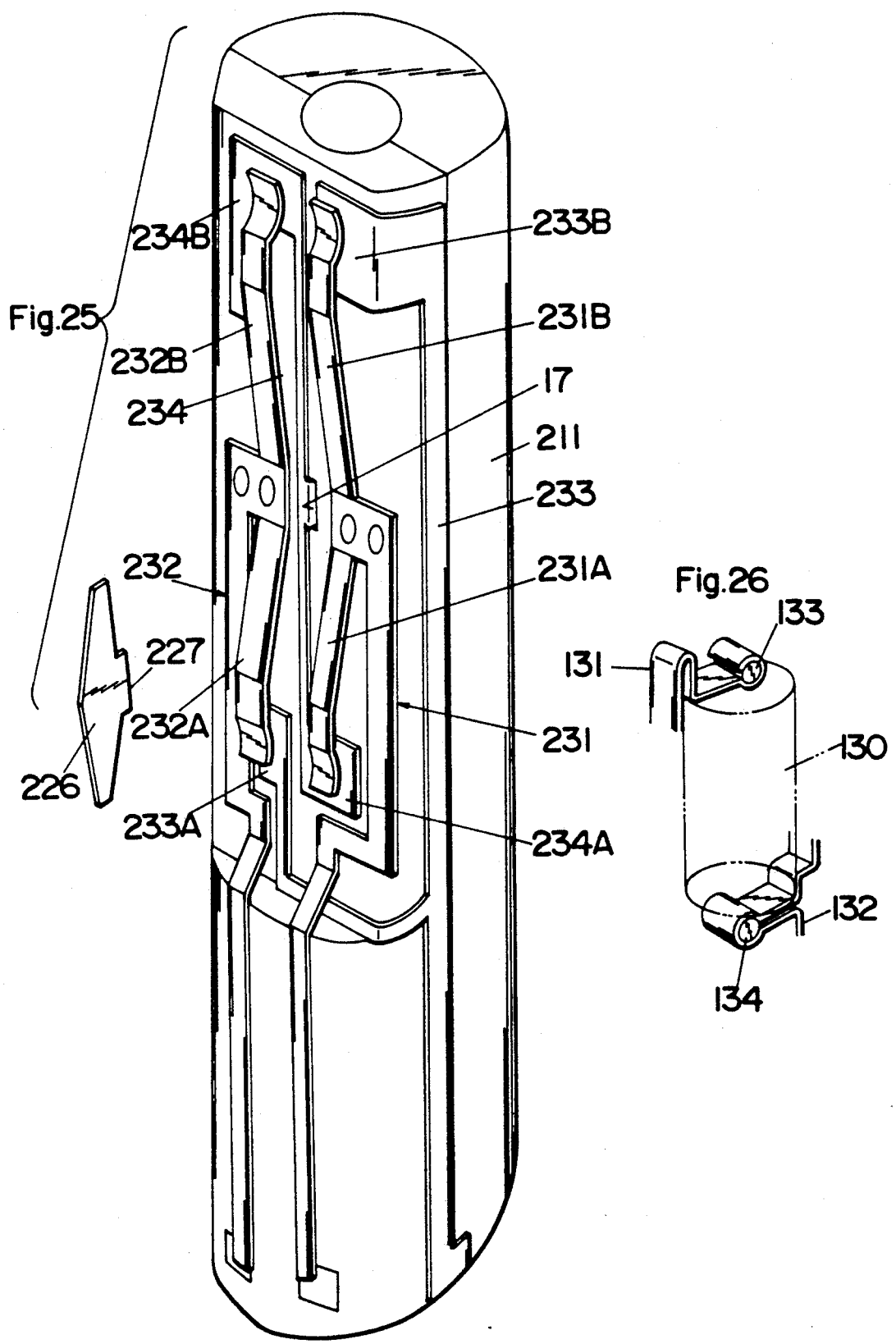

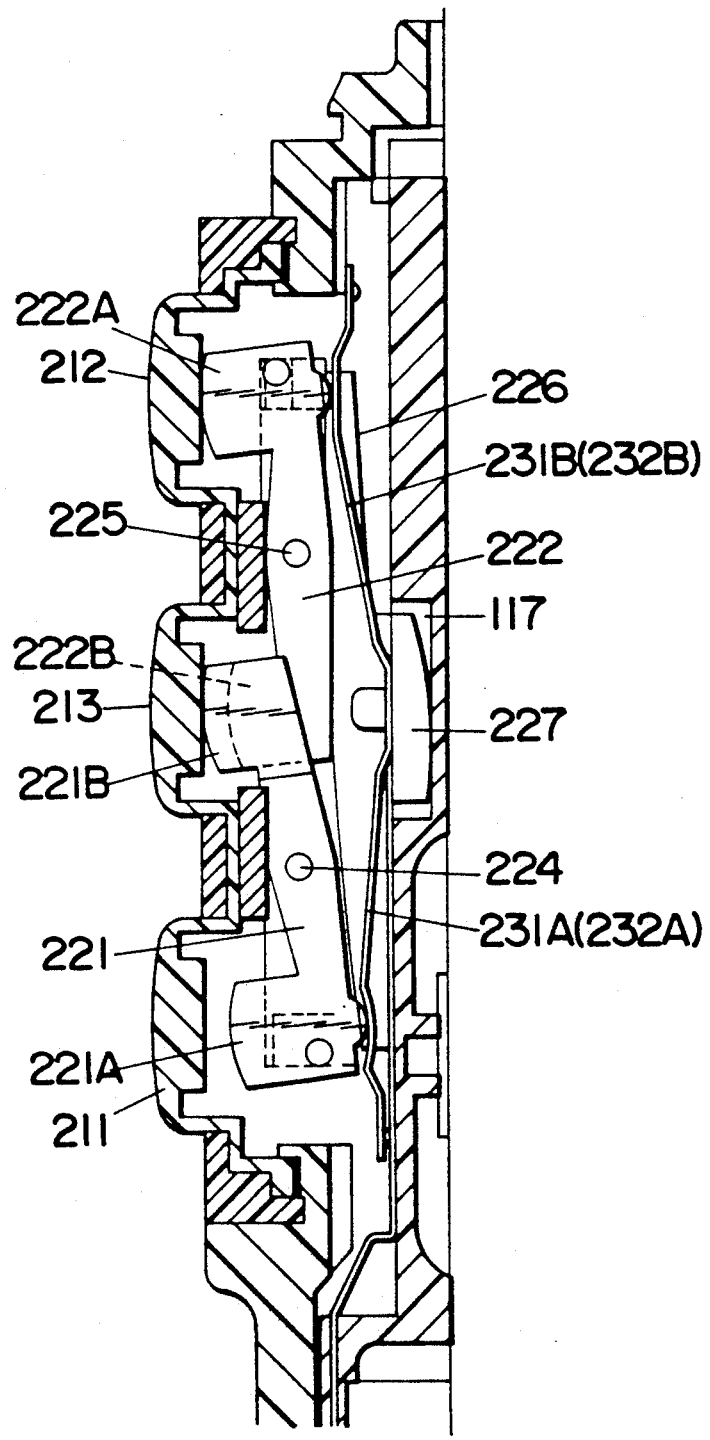

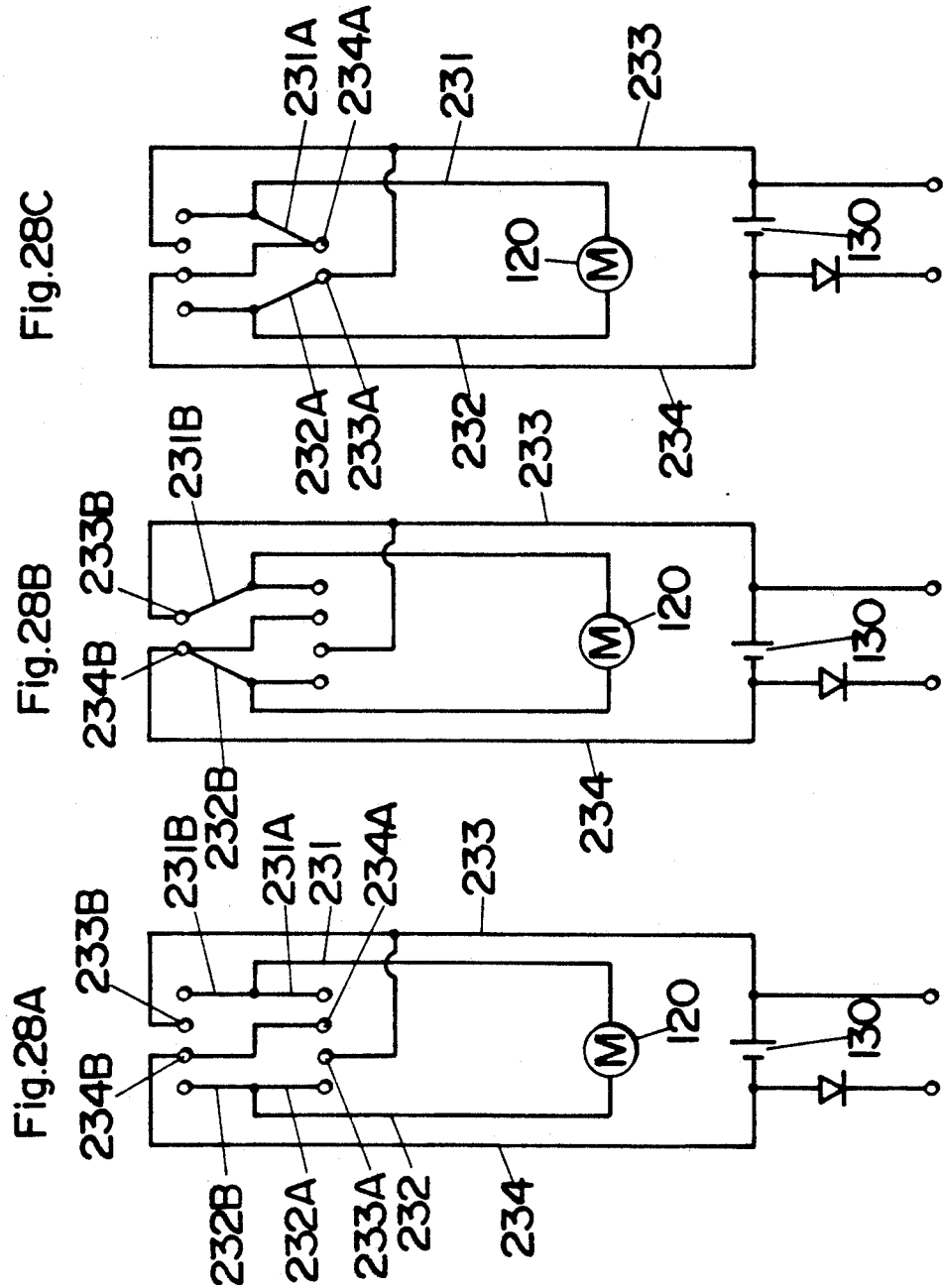

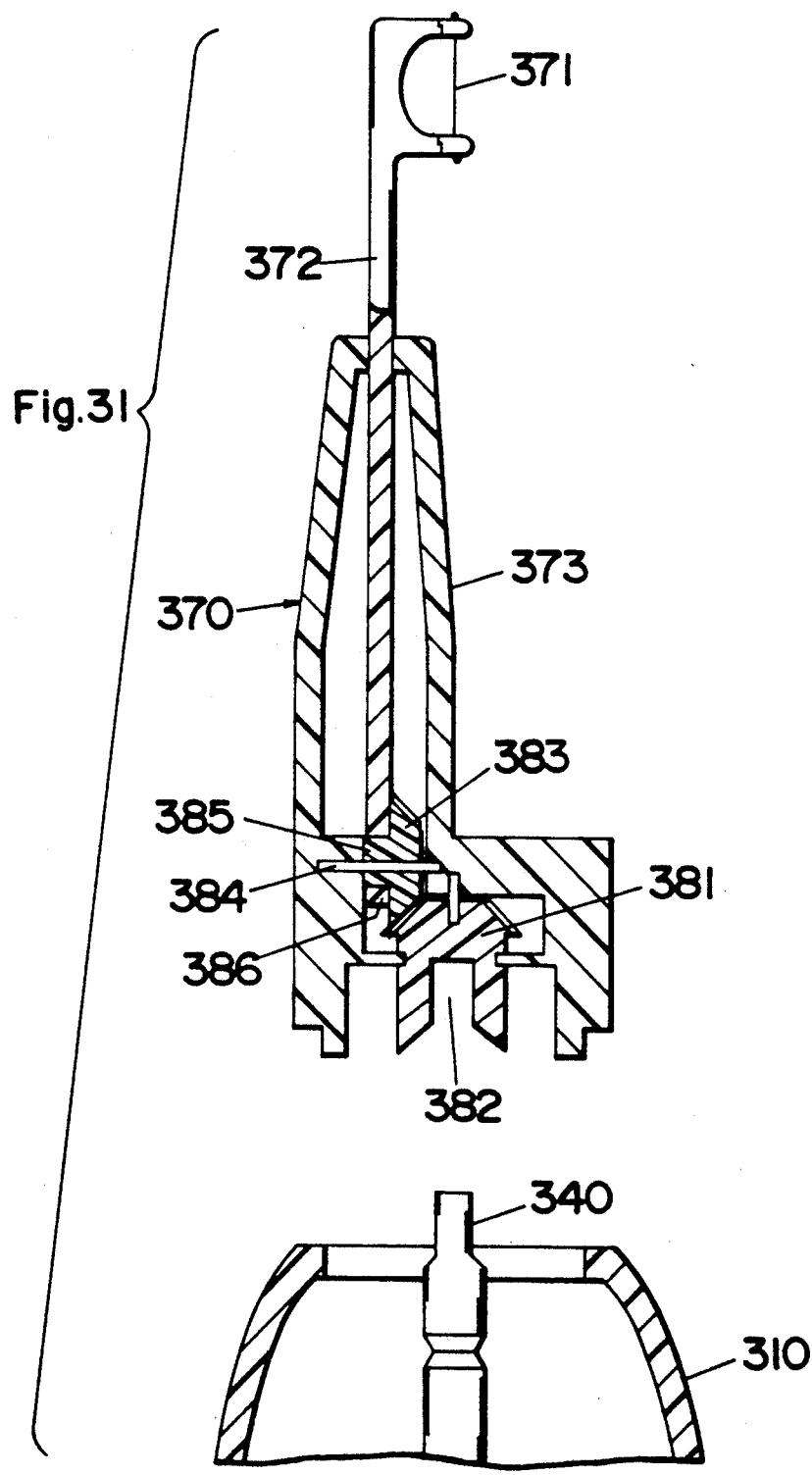

POWERED DENTAL FLOSS

BACKGROUND OF THE INVENTION

1. Field of the Invention

The present invention is directed to a powered dental floss, and more particularly to a powered dental floss driven by an incorporated motor to vibrate a floss along its length for an oral hygiene operation.

2. Description of the Prior Art

Manual dental floss has been provided in the art which comprises a handle and a floss in the form of a thread stretched between two forked ends of the handle. In order to effectively clean between the teeth by the floss, the user is required to vibrate the floss finely by repetitively and quickly moving one's hand gripping the handle. However, such manual operation of the dental floss produces fatigue of the wrist and of the fingers accumulating from repeated vibrations along the length of the floss, in addition to that the manual operation is difficult to impart a fine vibrating motion. Therefore, the manually operated dental floss is found still unsatisfactory in that it is cumbersome to use and is not expected to give a fine and effective vibration motion for interproximal cleaning.

SUMMARY OF THE INVENTION

The above problem has been avoided in the present invention which is capable of imparting a fine vibrating motion to a floss by a powered mechanism for effective interproximal cleaning operation. A powered dental floss in accordance with the present invention comprises a hand grip provided with an output shaft having a longitudinal axis and the floss connected to the output shaft as being stretched in a direction substantially parallel to the longitudinal axis of the output shaft. The hand grip incorporates a drive mechanism which is powered by an incorporated electric motor to cause the output shaft to vibrate along the longitudinal axis thereof, so that the floss is driven to vibrate substantially in the axial direction of the output shaft. Thus, it is readily possible to give a fine vibratory motion to the floss by the self-contained drive mechanism, thereby enabling effective interproximal cleaning without relying upon a cumbersome manual operation.

It is therefore a primary object of the present invention to provide a powered dental floss which is capable of achieving a fine vibratory motion of the floss and therefore easily performing effective interproximal cleaning.

In a preferred embodiment, the floss is stretched in alignment with the longitudinal axis of the output shaft for smooth vibratory motion of the floss. The floss is preferably driven to vibrate at a frequency of 1000 to 3500 cycles per minute with a stroke of 1.5 to 8.0 mm, which is found most effective and pleasant in removing teeth sordes in consideration of test results obtained from a number of monitors.

The floss is detachable to the output shaft so as to be replaced by a detachable toothbrush. Thus, the device of the present can be selectively utilized as a powered toothbrush simply by replacing the floss with the toothbrush, which is therefore another object of the present invention.

The drive mechanism is preferably designed to be capable of vibrating or swinging about the longitudinal axis of the output shaft, as well as vibrating along the longitudinal axis. In this case, the floss is preferred to be stretched in parallel with the longitudinal axis of the output shaft as being slightly offset therefrom so that the floss can oscillate about the longitudinal axis between the teeth for successfully scraping the sordes.

It is therefore a further object of the present invention to provide a powered dental floss which is capable of swinging the floss about an axis parallel to the length of the floss for effectively removing the sordes.

The powered dental floss additionally includes a load detector which monitors a load condition being applied to the motor and provides an output signal indicative of the monitored load condition. A controller, in response to the output signal, varies an operational speed of the output shaft and therefore varies the vibration rate of the output shaft in a direction of avoiding excess force being applied to the teeth and/or gums. Particularly, when an overload condition is detected, the controller responds to immediately cease the vibratory operation of the output shaft for safety purpose.

It is therefore a still further object of the present invention to provide a powered dental floss which is capable of preventing the floss from irritating and hurting the teeth and gums in a safety manner.

Further, the present invention discloses a unique supporting structure of capable of adjusting the orientation or angular disposition in relation to the longitudinal axis of the output shaft, and a unique mechanism of varying the vibration stroke.

These and still other objects and advantageous features of the present invention will become more apparent from the following description of the preferred embodiments when taken in conjunction with the attached drawings.

BRIEF DESCRIPTION OF THE DRAWINGS

FIG. 6 is an exploded perspective view of a portion of the drive mechanism including a face gear, a motor and the output shaft with a cam follower;

FIG. 7 is an exploded perspective view illustrating a bearing unit for supporting the output shaft in place within a hand grip;

FIG. 10 shows additional floss attachments selectively attached to the output shaft of the hand grip;

FIG. 11 is an exploded perspective view of another additional floss attachment which may be utilized in the present invention;

FIG. 12 is a perspective view of a further additional floss attachment which may be utilized in the present invention;

FIG. 13 is a front view illustrating the floss attachment of FIG. 12 with a floss held in an inclined position;

FIG. 14 is a sectional view taken along line 14—14 of FIG. 13;

FIG. 15 is an exploded perspective view of a still further additional floss attachment which may be utilized in the present invention;

FIG. 20 is a front view of a powered dental floss in accordance with a second embodiment of the present invention;

FIG. 21 is a perspective view of a hand grip of the dental floss of FIG. 20;

FIG. 22 is a perspective view, partly in section, of the above dental floss;

FIG. 23 is a vertical section of the above hand grip;

FIG. 24 is an exploded perspective view of a switch assembly utilized in the above dental floss;

FIG. 25 is a perspective view of a conductor circuit for the switch assembly of FIG. 24;

FIG. 26 is a schematic view illustrating the connection between the conductor circuit and a battery incorporated in the hand grip;

FIGS. 27A to 27C are respectively sectional views illustrating three operative positions of a switch handle;

FIGS. 28A to 28C are respectively circuit diagrams illustrating circuit conditions of the three switching positions in correspondence to FIGS. 27A to 27C;

FIG. 31 is an exploded vertical section of a powered dental floss in accordance with a third embodiment of the present invention.

DESCRIPTION OF THE PREFERRED EMBODIMENTS

Figure 1:
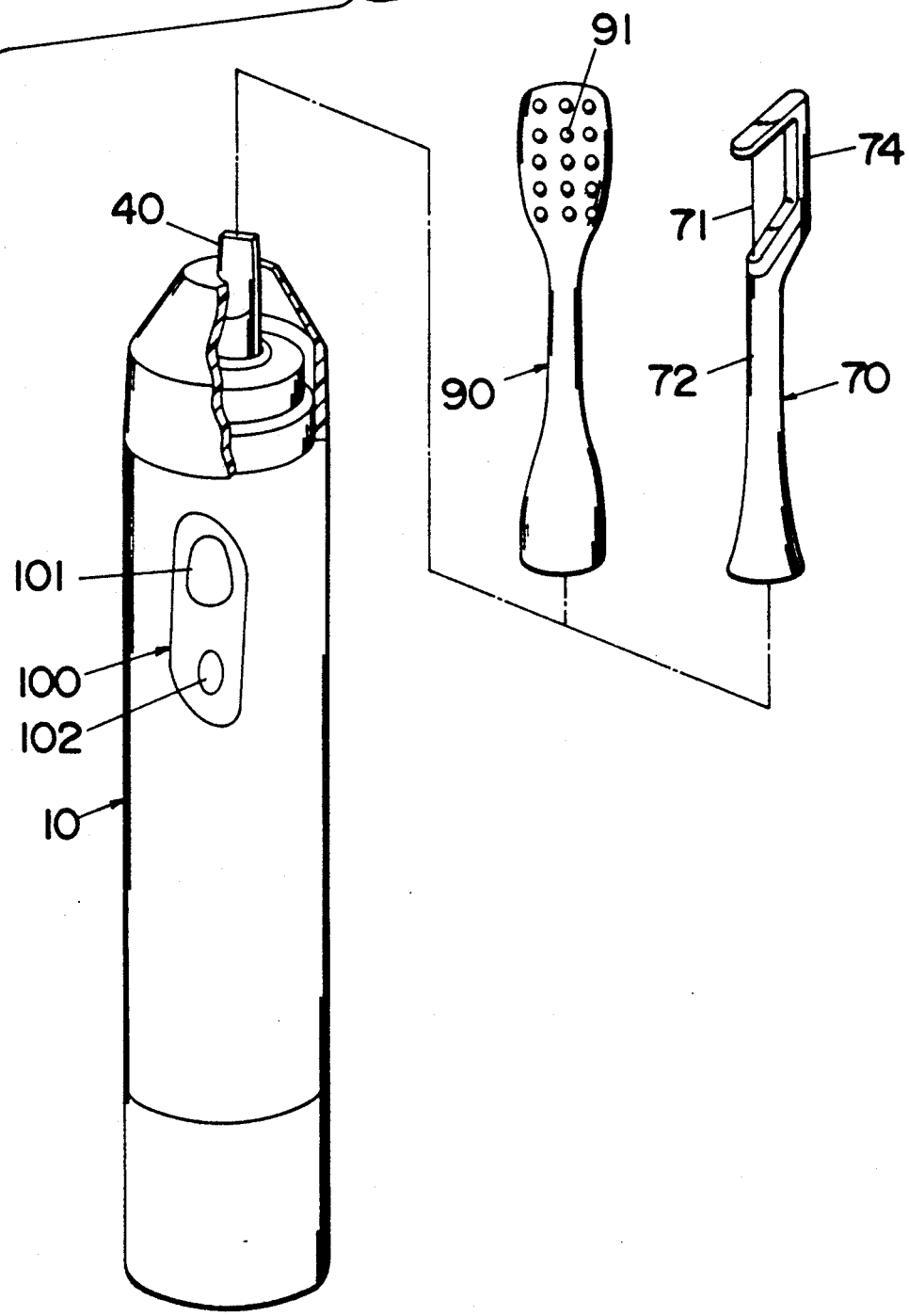
FIG. 1 is an exploded perspective view of a powdered dental floss in accordance with a first embodiment of the present invention.
Figure 2:
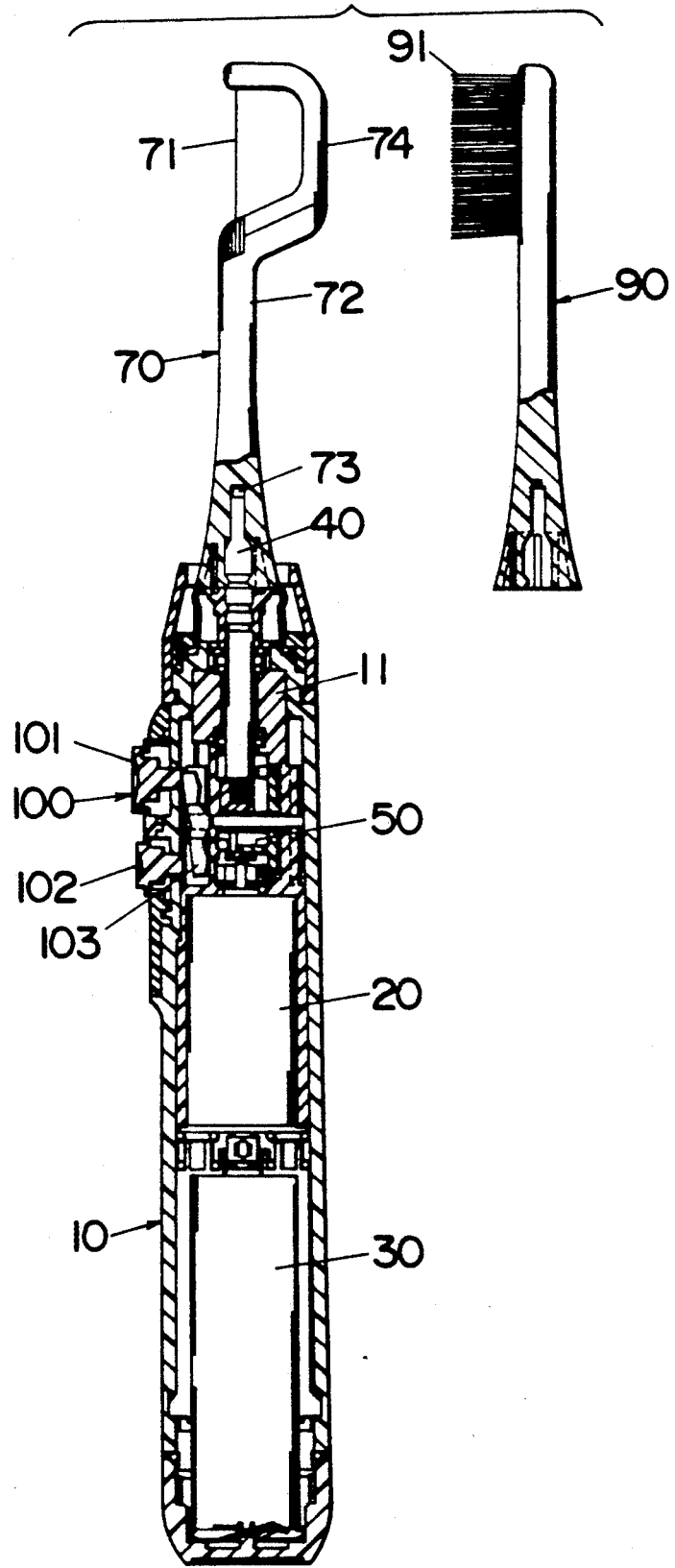
FIG. 2 is a vertical section of the dental floss.
Figure 3:
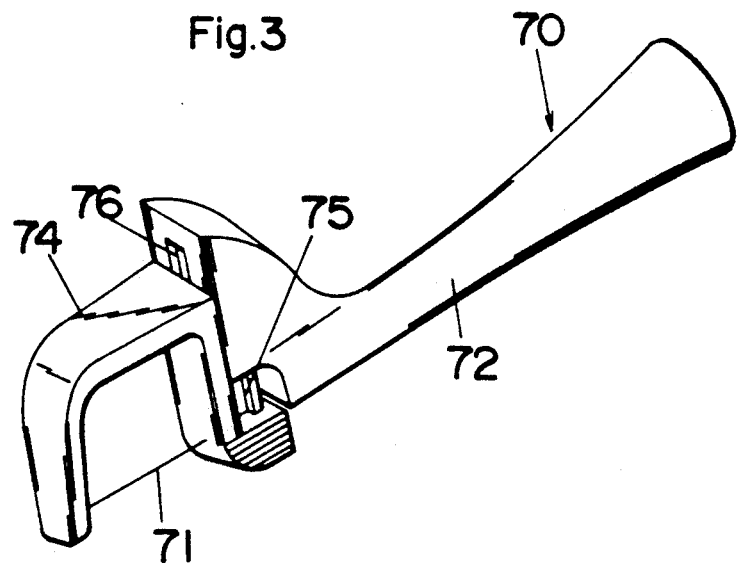
FIG. 3 is a perspective view of a floss attachment carrying a detectable floss holder.

Referring now to FIGS. 1 and 2, there is shown a powered dental floss in accordance with a first embodiment of the present invention. The dental floss comprises an elongated hand grip 10 of a generally cylindrical configuration incorporating therein an electric motor 20 and a rechargeable battery 30 energizing the motor 20. Projecting on the hand grip 10 is an output shaft 40 which has a longitudinal axis in alignment with a center axis of the hand grip 10 and is operatively connected to the motor 20 through a drive mechanism 50 so as to vibrate along the longitudinal axis. Detachably connected to the output shaft 40 is a floss attachment 70 carrying a floss 71 in the form of a thread stretched substantially in alignment with the longitudinal axis of the output shaft 40 so that the floss 70 is caused to vibrate in its axial direction. A toothbrush attachment 90 carrying a toothbrush 91 may be alternately coupled to the output shaft 40 when required. A switch 100 is mounted on and partly within the hand grip 10 to have a pair of vertically spaced ON- and OFF-buttons 101 and 102 exposed on the exterior of the hand grip 10. The switch 100 includes a rocker 103 which is engageable at its opposite ends respectively with the ON-button 101 and the OFF-button 102 to define a seesaw switch which is cooperative with switch contacts (not shown) to energize and deenergize the motor 20. The floss attachment 70 comprises a stem 72 formed in its lower end with a socket 73 for detachably receiving therein the output shaft 40 of the hand grip 10. Detachably attached to the upper end of the stem 72 is a holder 74 with a pair of forked ends between which the floss 71 is stretched in alignment with the longitudinal axis of the output shaft 40 of the hand grip 10. As shown in FIG. 3, the holder 74 is attached by sliding a guide projection 75 into a corresponding groove 76 in the upper end of the stem 72.

Figure 4:
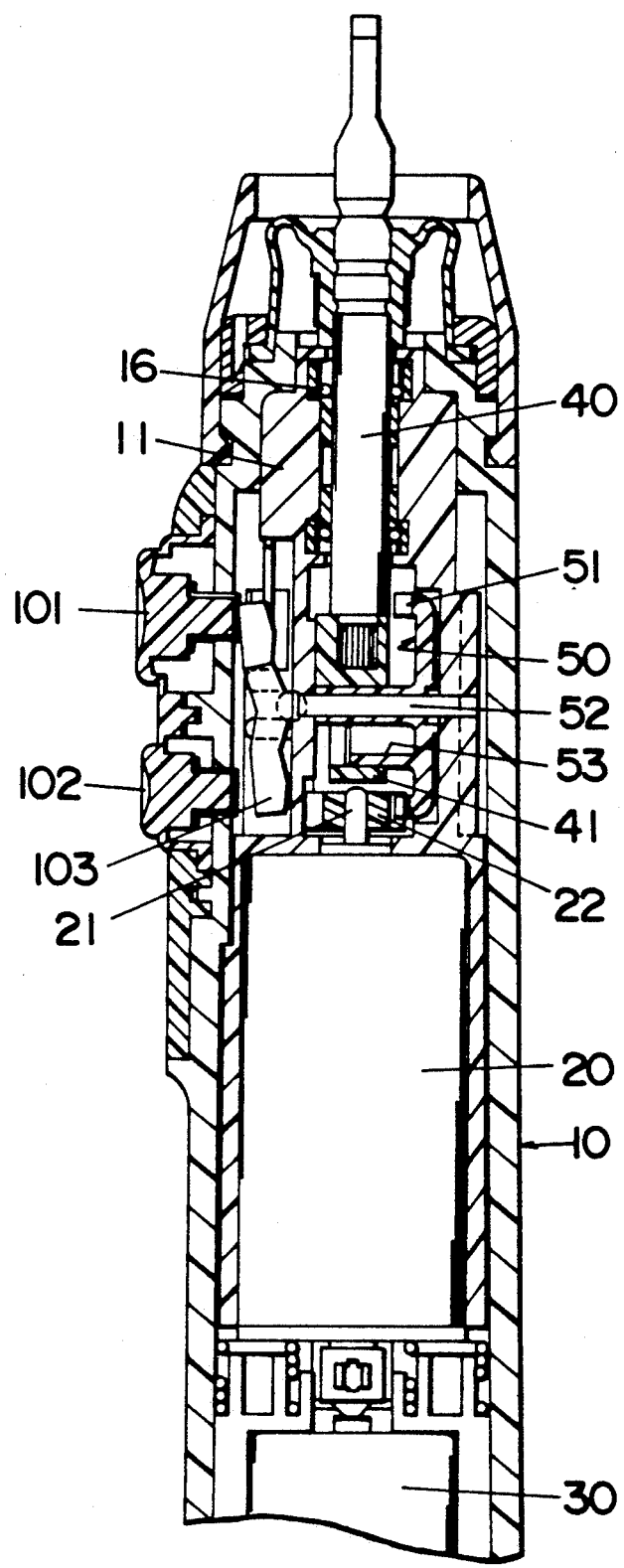
FIGS. 4 and 5 are vertical sections illustrating a drive mechanism of vibrating an output shaft along its longitudinal axis with the output shaft shown in the lowered and raised positions, respectively.
Figure 5:
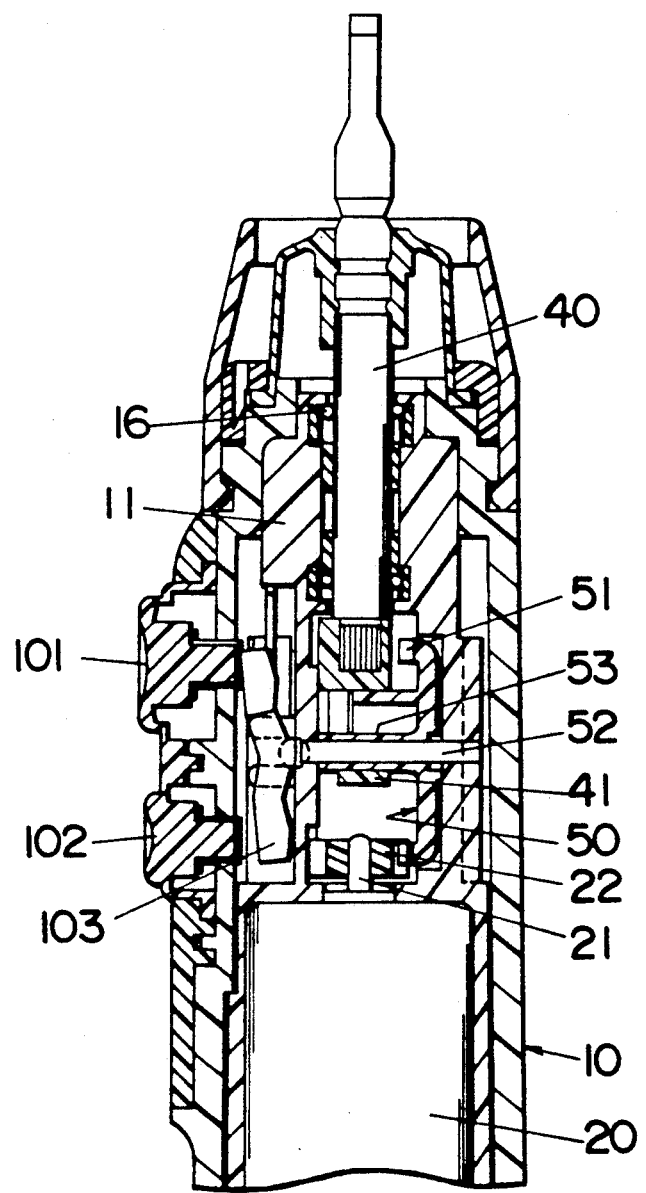

The output shaft 40 is supported by a frame 11 held within the upper end portion of the hand grip 10, as best shown in FIGS. 4 and 5. The frame 11 includes a pair of bearing units each comprising, as shown in FIG. 7, an outer sleeve 13 and an inner sleeve 14 carrying a number of balls 16 spaced circumferentially about the longitudinal axis of the output shaft 40 in rolling contact with the output shaft 40. The balls 16 are received respectively in circumferentially spaced and longitudinally extending slots 15 of the inner sleeve 14 so as to be movable therealong while being kept in rolling contact with the output shaft 40, thereby permitting the output shaft 40 to be movable along the longitudinal axis thereof.

The drive mechanism 50, which causes the output shaft 40 to vibrate along its longitudinal axis, comprises a face gear 51 in meshing engagement with a pinion 22 on a rotor shaft 21 of the motor 20, as shown in FIGS. 4 to 6. The face gear 51 is rotatably supported on a center shaft 52 extending horizontally with its opposite ends received in the frame 11 so as to be driven by the motor 20 to rotate about the center shaft 52. The face gear 51 also includes a cam barrel 53 extending horizontally in parallel with the center shaft 52 but having an axis eccentric to that of the center shaft 52. The cam barrel 53 extends into a cam follower 41 in the form of a ring provided at the lower end of the output shaft 40 such that the eccentric motion of the cam barrel 53 about the center shaft 52 is transformed into a vibratory motion of the output shaft 40 along its longitudinal axis. FIGS. 4 and 5 show the output shaft 40 in its lowered and raised positions, respectively. In this manner, the floss 71 connected to the output shaft 40 is driven to vibrate along its length, i.e., the longitudinal axis of the output shaft 40 for removing sordes between or around the teeth.

Figure 8:
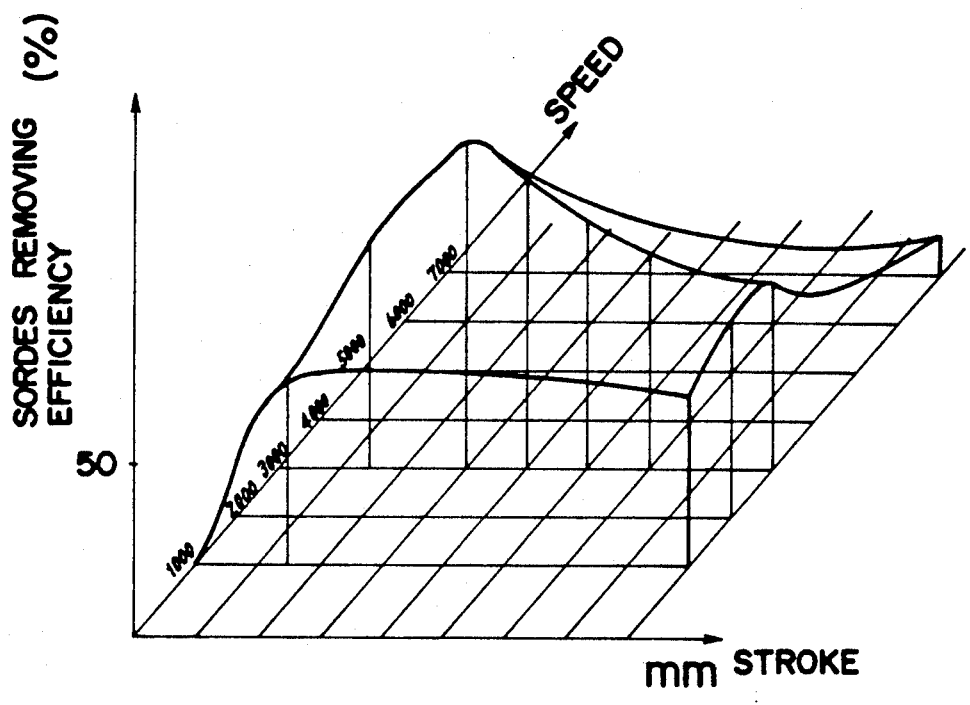
FIG. 8 is a 3-D graph illustrating sordes removal efficiency in relation to a vibration speed and a vibration stroke of the floss.
Figure 9:
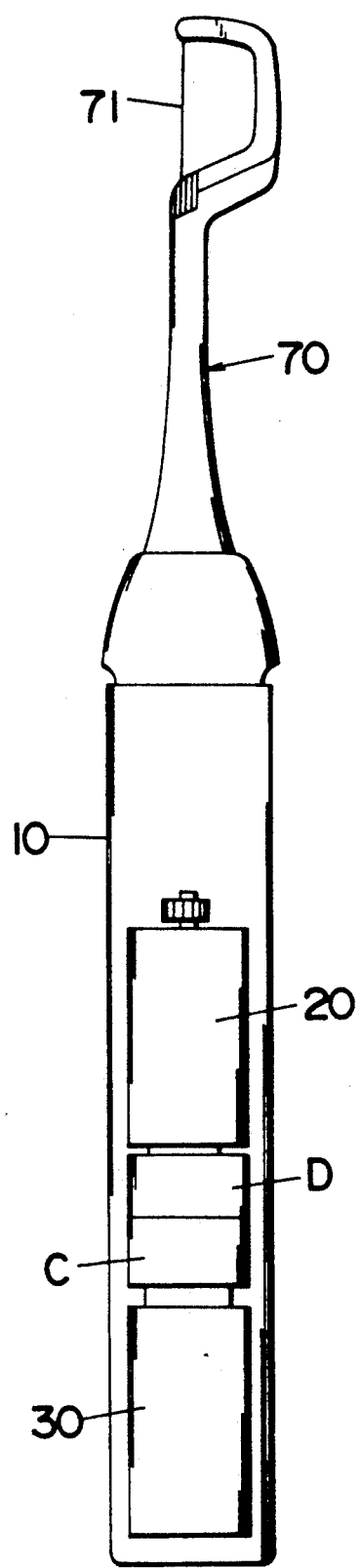
FIG. 9 is a schematic view of the above dental floss.
Figure 16:
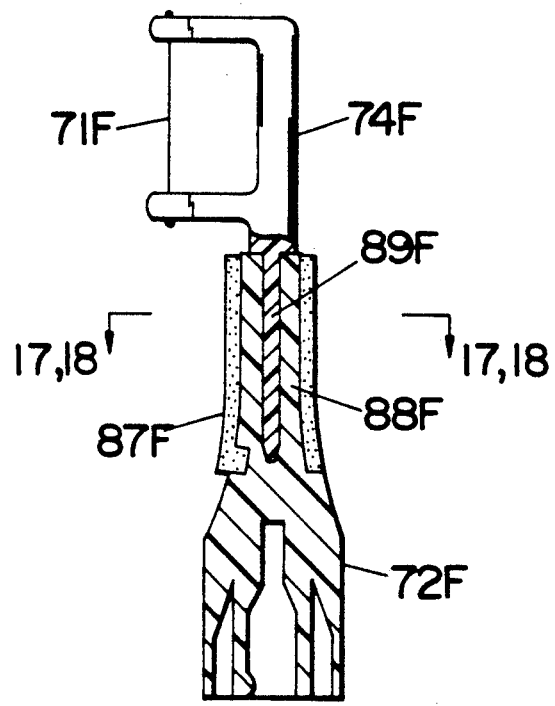
FIG. 16 is a vertical section, partly in elevation, of the floss attachment of FIG. 15.
Figure 17:
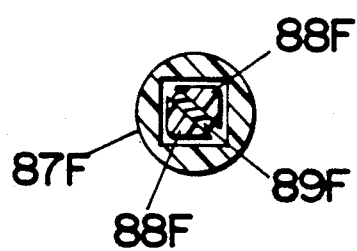
FIGS. 17 and 18 are sectional views taken along line 17,18—17,18 of FIG. 16, shown respectively in positions of loosely holding and locking a floss holder to the floss attachment.
Figure 18:
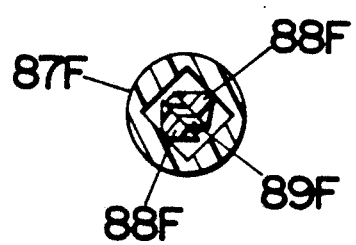

The output shaft 40 is preferred to vibrate at a frequency of 1000 to 3500 cycles per minute with a stroke of 1.5 to 8.0 mm which is found effective and pleasant in operation in view of investigations made for thirty (30) subjects as to sordes removing efficiency and convenience of using the dental floss. Sordes of the subjects were stained by a suitable dye for examining the sordes removing efficiency by a dental hygienist after operating to vibrate the floss 71 at given cycles and with give vibration strokes. The result is illustrated in FIG. 8, which reflects that:

1) only low sordes removing efficiency is seen with the vibration stroke of below 1.5 mm;
2) an extended time is required for attaining desired efficiency when vibrating the floss at a low speed of below 1000 cycles per minute;
3) vibrating the floss at an increased speed of above 3500 cycles per minute cause a violent vibration which is difficult to support by the user's hand; and 4) vibrating the floss with an increased stroke of exceeding 8.0 mm is harmful to the oral structure.

Taking into account for psychological effects as to manipulating convenience which the subjects felt in operating to vibrate the floss, the floss is found effective as well as pleasant in use when it is driven to vibrate at the above frequency range of 1000 to 3500 cycles per minute and within the above vibration stroke of 1.5 to 8.0 mm.

The hand grip 10 may incorporates a load detector D which is connected to the motor 20 for detection of a load being applied to the motor 20 as indicative of a load that the floss 71 suffers during the operation of vibrating the floss 71. The load detector D generates a corresponding output signal to a controller C which responds to control the rotation speed of the motor 20 in a feedback manner to vibrate the floss 71 at an optimum speed within the above range. When the load detector D detects an overload condition, it generates a stop signal to the controller C in order to immediately stop the motor 20 for avoiding to irritate or hurt the teeth and gums of the user by the floss 71.

As shown in FIG. 10, other types of floss attachments 70A to 70C may be utilized instead of the above floss attachment 70 or the toothbrush attachment 90. Included in the additional floss attachments are the floss attachment 70A with a floss 71A stretched in parallel with the longitudinal axis of the output shaft but in a horizontally offset relation thereto, the floss attachment 70B with a fixed floss 71B stretched in alignment with the longitudinal axis of the output shaft 40, and the attachment 70C with a floss 71C extending in a direction perpendicular to the longitudinal axis of the output shaft 40.

Another floss attachment 70D which may be utilized in the present invention is shown in FIG. 11 to comprises a stem 72D detachably mounting a holder 74D with a floss 71D. The holder 74D has a pin 77D rotatably fitted into a corresponding hole 78D in the upper end of the stem 72D and is locked in position by engagement of a hook 79D on the upper end of the stem 72D with a stepped shoulder 80D of the holder 74D.

FIGS. 12 to 14 show a further floss attachment 70E which may be utilized in the present invention. The floss attachment 70E comprises a holder 74E with a floss 71E held on the upper end of a stem 72E in such a manner that the floss 71E can be inclined with respect to the longitudinal axis of the stem 72E and therefore the output shaft 40 of the hand grip 10. To this end, the holder 74E has a swing leg 81E which extends into the upper end of the stem 72E and is pivoted at its lower end by means of a swivel pin 82E so that the holder 74E can swing about the swivel pin 82E. As shown in FIG. 14, the swing leg 81E is formed with a detent 83E which is engageable into any one of three recesses 84E formed in the upper end of the stem 72E so as to be latched at either of three positions in which the floss 71E extends in alignment with the longitudinal axis of the output shaft 40 or in inclined relation with respect thereto. The floss 71E is formed at its opposite ends with bulbs 85E and is stretched between forked ends of the holder 74E with the bulbs 85E engaged into correspondingly formed notches 86E in the forked ends.

A still other modified floss attachment 70F is shown in FIGS. 15 to 18 to comprises a holder 74F with a floss 71F which is detachably supported to a stem 72F by means of a sleeve 87E having a bore of square cross section. The stem 72F is formed in its upper end with bifurcated extensions 88F of triangular cross-section which are resiliently deformable and define therebetween a slit into which a planar extension 89F of the holder 74F extends. The sleeve 87F is fitted around the bifurcated extensions 89F and is rotatable thereabout between a loose position of FIG. 17 in which the bifurcated extensions 88F are out of engagement with the inner surfaces of the sleeve 87F and a lock position of FIG. 18 in which the bifurcated extensions 88F are urged inwardly by the inner surfaces of the sleeve 87F to tighten the planar extension 89F between the bifurcated extensions 88F. Thus, the holder 74F can be easily locked to the stem 72F simply by inserting the planar extension 89F between the bifurcated extensions 88F and rotating the sleeve 87F by an angle of 90°.

Figure 19:
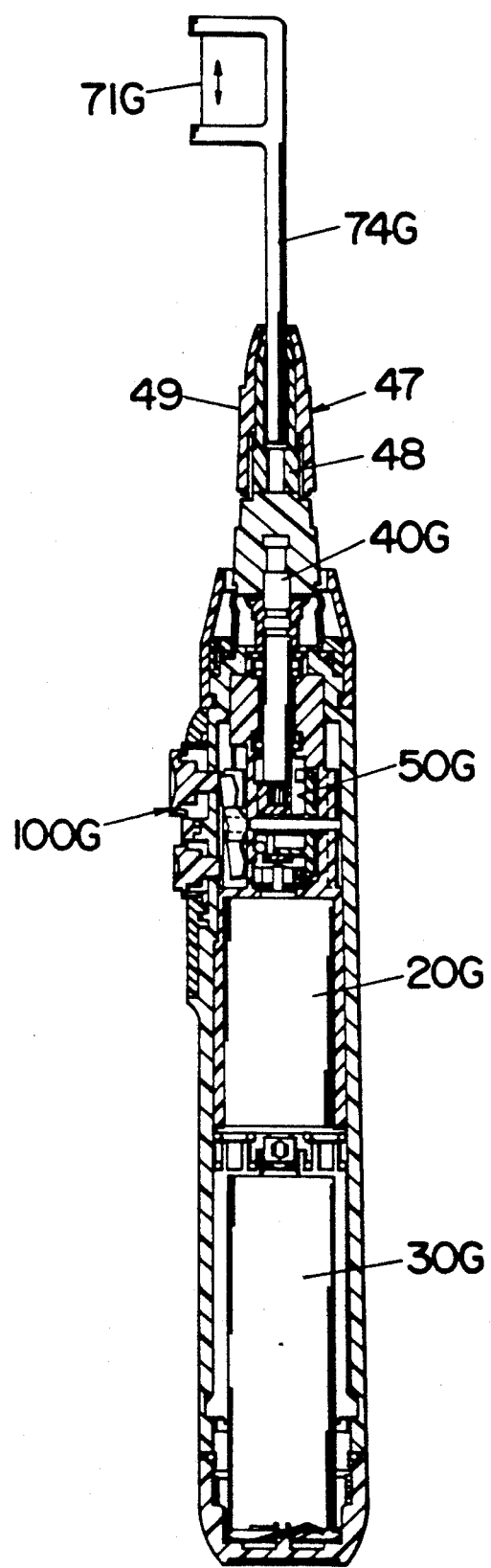
FIG. 19 is a vertical section of a powered dental floss in accordance with a first modification of the above embodiment.

FIG. 19 is a modification of the above embodiment which is identical in structure and operation to the above embodiment except that an output shaft 40G is additionally provided with a collet-type chuck 47 for detachably mounting a commercially available floss holder 74G having a straight handle with a floss 71G stretched between forked ends at the upper end of the handle. Like parts are designated by like numerals with a suffix letter of "G". The chuck 47 comprises a barrel 48 which is rotatable together with the output shaft 40G and into which the handle of the holder 74G extends. The barrel 48 is circumferentially divided into a plurality of radially displaceable sections with external thread at the respective lower ends. Fitted around the barrel 48 is a cap 49 which comes into threaded engagement at its lower portion with the barrel 48 and which has an upper end portion tapered axially for pressing engagement with the upper end of the barrel 48. Thus, the barrel 48 can be tightened on the handle of the holder 74G simply by rotating the cap 49 around the barrel 48.

Referring to FIGS. 20 and 21, there is shown a powered dental floss in accordance with a second embodiment of the present invention which comprises a hand grip 110 with an upwardly projecting an output shaft 140 having a longitudinal axis concentric with a center vertical axis of the hand grip 110. The output shaft 140 is driven by an incorporated drive mechanism 150 to vibrate along the longitudinal axis as well as to vibrate or swing thereabout selectively in accordance with the rotational direction of a motor 120. A floss attachment 170 detachably connected to the output shaft 140 has a floss 171 stretched in parallel with the longitudinal axis but is offset by a slight extent of "e" therefrom for giving a rolling motion to the floss when it is driven to vibrate about the longitudinal axis of the output shaft 140, as discussed later The hand grip 110 is provided with a switch assembly including three buttons, namely, a first button 211 for rotating the motor 120 in one direction to effect vibrating the floss 171 along the longitudinal axis of the output shaft 140, a second button 212 for rotating the motor 120 in the opposite direction to effect vibrating the floss 171 about the longitudinal axis of the output shaft 140, and a stop button 213 for deenergizing the motor 120. Also in this embodiment, the toothbrush attachment 90 may be coupled to the output shaft 140 instead of the floss attachment 170 to effect brushing by vibrating the toothbrush either along or about the longitudinal axis of the output shaft 140.

The drive mechanism 150 in this embodiment is provided to transform a rotary motion of the motor 120 into the vibrating motion of the output shaft 140 along and about the longitudinal axis thereof in response to the motor 120 rotating in one direction and the other direction, respectively. To this end, the drive mechanism 150 comprises a face gear 151 in meshing engagement with a pinion 122 on a rotor shaft 121 of the motor 120, as shown in FIG. 23. The face gear 151 is rotatably supported on a center shaft 152 extending horizontally with its opposite ends received in a chassis 111 so as to be driven by the motor 120 to rotate about the center shaft 152. The face ear 151 also includes an eccentric axle 153 extending horizontally in parallel with the center shaft 152 but having an axis eccentric to that of the center shaft 152. Fitted around the eccentric axle 153 is a cam barrel formed with a pair of axially spaced first and second cams 155 and 156 which are circumferentially offset to each other about an eccentric axis of the barrel. The first and second cams 155 and 156 are permitted to freely rotate about the eccentric axle by a limited angular range of 180° and are engaged respectively with first and second cam followers 141 and 142 formed at the end of the output shaft 140 such that, when the face gear 151 rotates in one direction, the first cam 155 comes into engagement with the first cam follower 141 so as to vibrate the output shaft 140 vertically along the longitudinal axis thereof while the second cam follower 142 is kept free from the second cam 156 and that, when the fact gear 151 rotates in the opposite direction, the second cam 156 comes into engagement with the second cam follower 142 to vibrate the output shaft 140 about its longitudinal axis while the first cam follower 141 is kept free from the first cam 155. The detailed operation and structure of the drive mechanism 150 have been disclosed in our invention published as Japanese Patent Early Publication No. 62-295610 published on Dec. 23, 1987 and therefore further explanation herein is not deemed necessary. The chassis 111 includes a cylinder 112 which has a pair of bearings 113 supporting the output shaft 140 for smoothly guiding it to vibrate either along or about the longitudinal axis thereof.

As shown in FIG. 24, the switch assembly includes a handle plate 210 which is fitted into a notch 116 in a casing of the hand grip 110 and which is made of a rubber to integrally form thereon the above three buttons 211 to 213. A seal cover 214 is fitted over the handle plate 210 to the casing by a suitable welding. Disposed behind the handle plate 210 is a switch frame 220 which is also secured into the notch 116 of the casing by means of rearwardly extending hooks 229. The switch frame 220 carries a pair of first and second actuators 221 and 222 which are vertically spaced and have their middle portions pivotally supported by means of pivot pins 224 and 225, respectively. The first actuator 221 is formed at its lower end with a circular bump 221A which is positioned immediately behind the first button 211 such that pushing in of the first button 211 causes the first actuator 221 to pivot about the pivot pin 224 in one direction. Likewise, the second actuator 222 is formed at its upper end with a circular bump 222A which is positioned immediately behind the second button 212 such that pushing in of the second button 212 causes the second actuator 222 to pivot about the pivot pin 225 in one direction. The first and second actuators 221 and 222 are formed respectively at the respective ends opposite of the bumps 221A and 222A with semicircular bumps 221B and 222B which are disposed in side-by-side relation and positioned immediately behind the stop button 213 such that pushing in of the stop button 213 cause the first and second actuators 221 and 222 together to pivot about the respective pivot pins 224 and 225 in the opposite directions. Formed at each of the upper and lower ends of the switch frame 220 are dents 226 (only those at the upper end of the frame 220 are seen in FIG. 24) which are spaced by a ridge for selectively receiving a side flange 227 correspondingly formed at each one of the first and second actuators 221 and 222 such that the first and second actuators 221 and 222 can be latched in two positions, namely a neutral position and the pressed-in position. Cooperative with the first and second switch actuators 221 and 222 is a conductor circuit which comprises, as shown in FIG. 25, four conductors 231 to 234 formed on the chassis 111 The first and second conductors 231 and 232 are connected at their lower ends electrically to input terminals of the motor 120, respectively, while the third and fourth conductors 233 and 234 are connected at the respective ends electrically to positive and negative electrodes of a battery 130, respectively by way of terminal members 131 and 132, as shown in FIG. 26. At portions held in contact with the electrodes of the battery 130 the terminal members 131 and 132 are formed with loops holding elastic pads 133 and 134 by which the loops are urged into pressed contact with the corresponding electrodes.

Figure 27A:
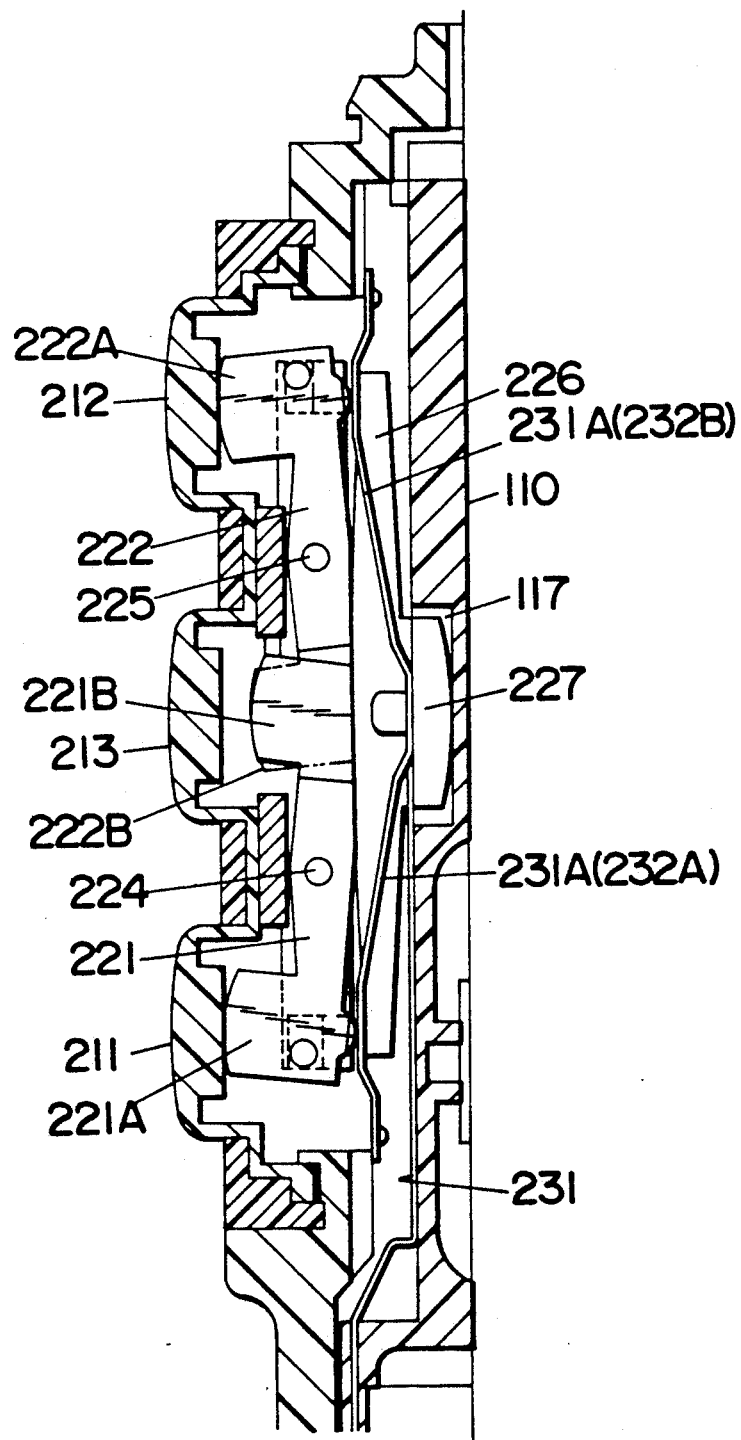
Figure 27B:
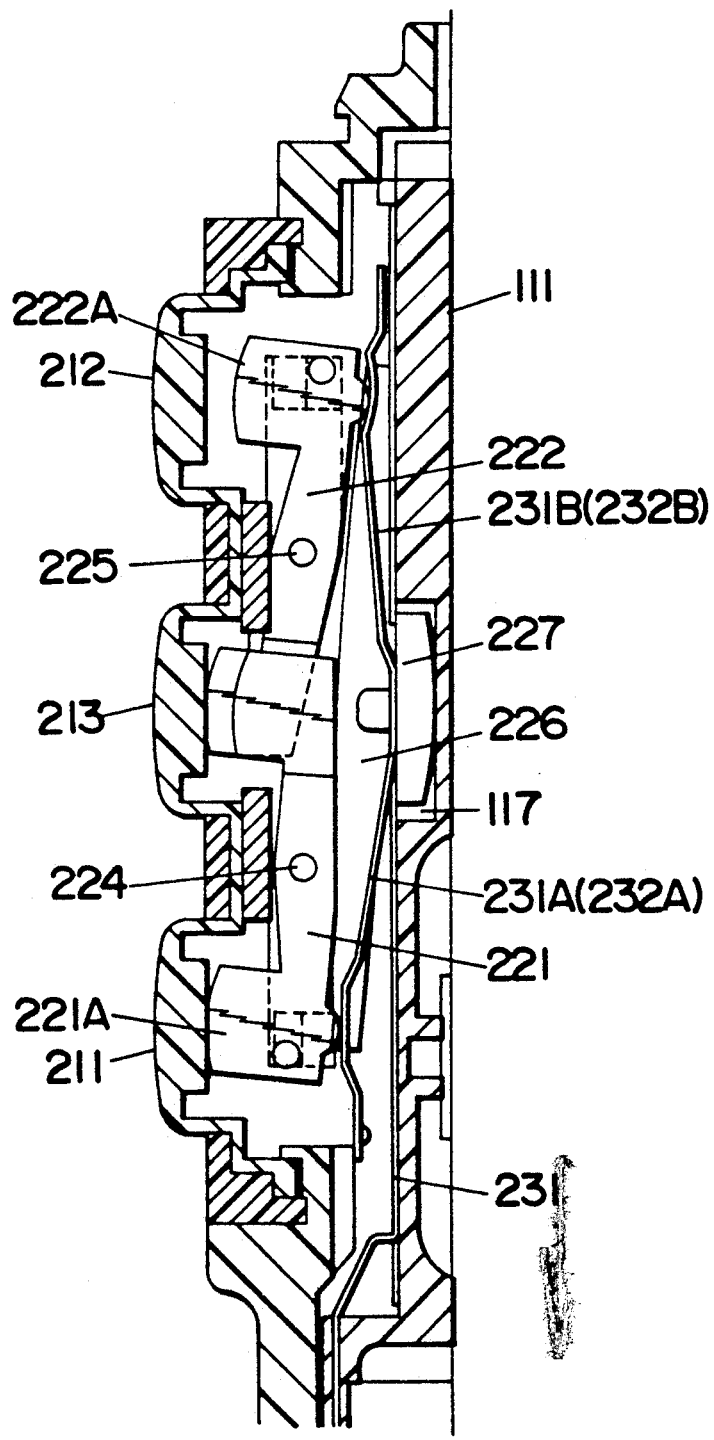

Turning back to FIG. 25, the first and second conductors 231 and 232 are formed integrally with sets of lower and upper spring legs 231A and 231B, 232A and 232B arranged in such a relation that the lower and upper spring legs of the first conductor 231 extend in close parallel relation to those of the second conductor 232, respectively. The lower spring legs 231A and 232A of the first and second conductors 231 and 232 have their respective free ends kept normally in open circuit condition from corresponding tabs 234A and 233A of the fourth and third conductors 234 and 233, respectively. Likewise, the upper spring legs 231B and 232B of the first and second conductors 231 and 232 have their respective free ends kept normally in open circuit condition from corresponding tabs 233B and 234B of the third and fourth conductors 233 and 234, respectively. As shown in FIG. 27A, the lower and upper spring legs 231A (232A) and 231B (232B) are spring biased into abutment respectively with the first and second actuators 221 and 222 to retain them at their neutral positions, respectively. This open circuit condition is shown in FIG. 28A where the motor 120 is kept disconnected from the battery 130. When the first button 211 is pressed in, the lower springs 231A and 232A are together pressed through the first actuator 221 to come into closed circuit condition with the corresponding tabs 233B and 234B of the third and fourth conductors 233 and 234, respectively. When the first button 211 is pressed in, the lower springs 231A and 232A are together pressed through the first actuator 221 to come into closed circuit condition with the corresponding tabs 234A and 233A of the fourth and third conductors 234 and 233, respectively, as shown in FIGS. 27C and 28C. Whereby the motor 120 is connected to the battery 130 so as to rotate in one direction, in this instance, for vibrating the output shaft 140 along its longitudinal axis. On the other hand, when the second button 212 is pressed in, the upper springs 231B and 232B are together pressed through the second actuator 222 to come into closed circuit condition with the corresponding tabs 233B and 234B of the third and fourth conductors 233 and 234, respectively, as shown in FIGS. 27B and 28B. Whereby the motor 120 is also connected to the battery 130 but in the opposite polarity so as to rotate in the opposite direction, in this instance, for vibrating the output shaft 140 about its longitudinal axis. Also included in the switch assembly is a swing lever 226 which, as shown in FIGS. 25 and 27A to 27C, is supported on the chassis 111 with its rear projection 227 engaged into a corresponding slot 117 so as to be movable in seesaw fashion. The lever 226 is engaged at its lower and upper inclined front edges respectively with the first and second actuators 221 and 222 so that it is caused to swing in response to the pressing-in of either of the first actuator 221 or second actuator 222, i.e., the first button 211 or second button 212. Whereby, upon pressing-in of the first button 211 at a condition of FIG. 27B where the second button 212 is previously pressed in to keep the motor 120 rotating, the swing lever 226 acts to forcibly return the second actuator 222 to the neutral position, thus permitting the upper spring legs 231B and 232B of the first and second conductors 231 and 232 to be disengaged from the corresponding tabs 233B and 234B, and therefore making it possible to reverse the motor 120 without requiring an intermediate step of pressing-in of the stop button 213. Likewise, upon pressing-in of the second button 212 at a condition of FIG. 27C where the first button 211 is previously pressed in and the motor 120 is kept rotating, the swing lever 226 responds to deactivate the motor 120 automatically before reversing the motor 120. In this manner, the motor 120 can be reversed quickly by simply pressing either of the first button 211 or second button 212 so that the user can quickly switch between the two operation modes of vibrating the floss 171 along and about the longitudinal axis of the output shaft 140.

Figure 29A:
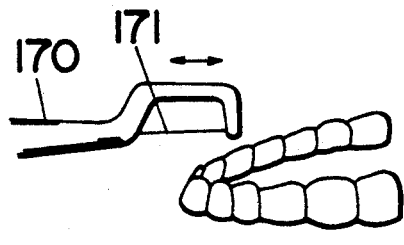
FIGS. 29A to 29C are schematic views illustrating the operations of the floss in relation to the teeth, respectively.
Figure 29B:
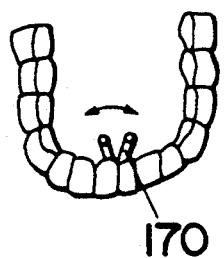
Figure 29C:
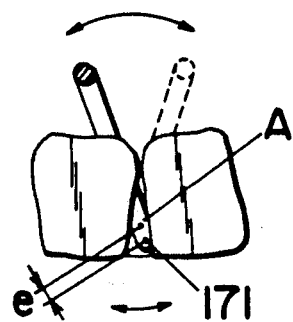

Since the output shaft 140 of this embodiment can be driven to selectively Vibrate along and about the longitudinal axis thereof depending upon the rotational directions of the motor 120, the floss 171 may be operated to vibrate along its stretched direction, as shown in FIG. 29A and to vibrate in an eccentric manner about the longitudinal axis of the output shaft 140 to effect rolling motion, as shown in FIG. 29B. In this operation mode, the floss 171 is caused to roll about the longitudinal axis A of the output shaft 140, as shown in FIG. 29C, between the teeth by an amount corresponding to the eccentricity "e" of the floss 171 to the axis A thereby effectively scraping the sordes or the like on the sides of the teeth. The above rolling motion of the floss 171 is particularly suitable and advantageous for scraping the sordes around the roots of the teeth since the floss 171 is easy to swing over a long distance between the roots of the teeth where the interproximal distance is wider toward the roots than at the upper end, as best shown in FIG. 29C. It should be noted at this time that the floss 171 can be easily placed between the teeth when driven to vibrate along its length, as shown in FIG. 29A.

Figure 30A:
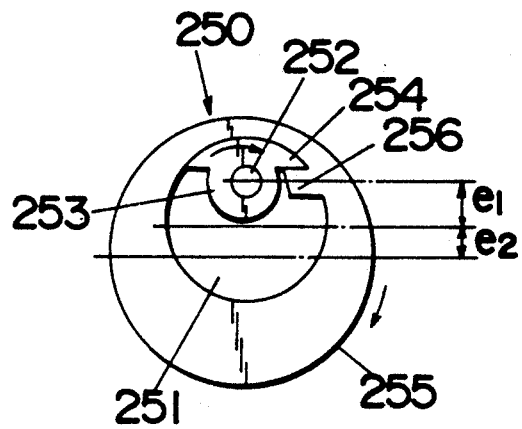
FIGS. 30A and 30B are schematic views illustrating a cam drive mechanism for varying a vibration stroke of the output shaft depending upon the rotational direction of an incorporated motor.
Figure 30B:
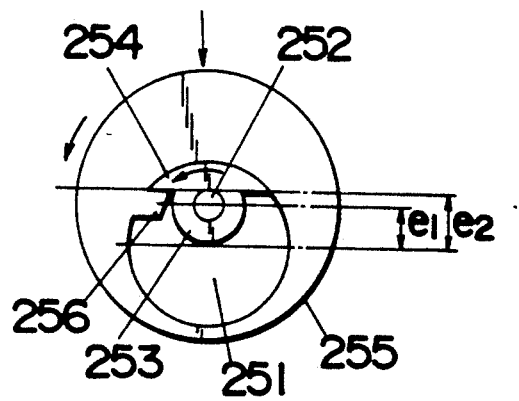

Although the output shaft 140 is made in this embodiment to vibrate selectively along and about the longitudinal axis thereof depending upon the rotational direction of the motor 120 by the use of the drive mechanism 150, the present invention should be understood to encompass another important feature of varying the vibration stroke in accordance with the changing rotational direction of the motor 120. This is accomplished by using a uniquely configured cam drive mechanism 250, as shown in FIGS. 30A and 30B, in place of the above drive mechanism 150. The cam drive mechanism 250 comprises an eccentric sleeve 251 rotatable about a center shaft 252 of a face gear which is identical to that 51 utilized in the first embodiment and is in meshing engagement with a corresponding pinion of the motor 20. The eccentric sleeve 251 has its own axis which is eccentric to that of the center shaft 252 by a distance of $e_1$ and is driven to rotate together with the face gear about the center shaft 252. Formed at the axial end of the eccentric sleeve 251 is an axially projecting post 253 with a radial extension which defines a pair of shoulders 254 spaced circumferentially about the center shaft 252 by an angle of 180°. Fitted around the eccentric sleeve 251 is an eccentric cam 255 in the form of a cylinder which has its own axis eccentric to that of the eccentric sleeve 252 by a distance of $e_2$ which is not equal to $e_1$ of the sleeve 251 in relation to the center shaft 252. The eccentric cam 255 includes an inwardly projecting stop 256 which is engageable with either of the shoulders 254 such that the eccentric cam 255 is rotatable over a limited angular range of about 180° in relation to the sleeve 251 between a first position of FIG. 30A in which the stop 256 engages with one of the shoulders 254 and a second position of FIG. 30B in which the stop 256 engages with the other shoulder 254. The eccentric cam 255 is confined within a like cam follower as that 41 utilized in the first embodiment to transform an eccentric rotation of the cam 255 into a vibrating motion of a corresponding output shaft along its length. As shown in FIG. 30A, when the sleeve 251 is driven by the motor to rotate in a clockwise direction as indicated by a arrow in the figure, the cam 255 is forced to rotate together in the same direction by engagement of the stop 256 and the shoulder 254 with an added eccentricity of $e_1+e_2$ in relation to the center shaft 252, thereby resulting in a correspondingly great vibration stroke of the output shaft. On the Other hand, when the sleeve 251 is driven to rotate in the counterclockwise direction, it rotates within the cam 255 until the other shoulder 254 comes into abutment with the stop 256, i.e., from the first position of FIG. 30A to the second position of FIG. 30B, where the cam 255 has a reduced eccentricity of $e_2-e_1$ in relation to the center shaft 252. Thereafter, the cam 255 is forced to rotate together with the sleeve 251 in the same direction with the reduce eccentricity, thereby causing the output shaft to vibrate at a correspondingly reduced stroke. Thus, with the provision of giving different eccentricities $e_1$ and $e_2$ to the sleeve 251 and the cam 255 in the above drive mechanism, it is readily possible to vary the vibration stroke simply by changing the rotational direction of the motor.

A third embodiment of the present invention is shown in FIG. 31 to comprise a hand grip 310 and a floss attachment 370. The hand grip 310 includes an output shaft 340 which is driven to vibrate about its longitudinal axis by an incorporated motor through a driven mechanism (not shown). The floss attachment 370 includes a stem 372 carrying a floss 371 and a holder 373 for slidably supporting the stem 372. The floss 371 is stretched in a direction parallel to the stem 372. Included in the holder 373 is a motion-converter comprising a set of bevelled gears 381 and 383 for converting the vibration of the output shaft 340 about its axis into a vibration of the stem 372 and the floss 371 along the lengthwise direction thereof. One of the bevelled gears has a socket 382 into which the output shaft 340 engages. The other bevelled gear 383 in meshing engagement with the gear 381 is supported on a horizontal axle 384 and has an integral cam shaft 385 which is engaged into a cam follower 386 in the form of a ring provided at the lower end of stem 372 so that the floss 371 is driven to vibrate along its axis. In order to vibrate the floss 371 in the direction, the output shaft 340 needs not to be vibrate about its axis and may alternately rotate about the axis.

What is claimed is:

1. A powered dental floss comprising:
a hand grip provided with an output shaft having a longitudinal axis, said hand grip incorporating a motor and a drive mechanism powered by said motor to cause said output shaft to vibrate along said longitudinal axis;
a floss connected to said output shaft and stretched to extend in a direction substantially parallel to and in alignment with said longitudinal axis so as to be driven by said output shaft to vibrate in that direction.

2. A powered dental floss as set forth in claim 1, said drive mechanism vibrates said floss with a stroke of 1.5 to 8.0 mm and at a frequency of 1000 to 3500 cycles per minute.

3. A powered dental floss as set forth in claim 1, wherein said floss is detachably coupled to said output shaft.

4. A powered dental floss comprising:
a hand grip provided with an output shaft having a longitudinal axis, said hand grip incorporating a drive mechanism powered by a motor to cause said output shaft to vibrate or rotate about said longitudinal axis;
an attachment carrying a floss and being detachably connected to said output shaft, said attachment including a motion-converting mechanism which converts the motion of said output shaft about its longitudinal axis into a vibrating motion of said floss in a direction parallel to said longitudinal axis of said output shaft.

5. A powered dental floss comprising:
a hand grip provided with an output shaft having a longitudinal axis, said hand grip incorporating a motor and a drive mechanism powered by said motor to cause said output shaft to vibrate along said longitudinal axis;
(a) a floss connected to said output shaft and stretched to extend in a direction substantially parallel to said longitudinal axis so as to be driven by said output shaft to vibrate in that direction;
(b) a toothbrush selectively detachable to said output shaft in place of said floss.

6. A powered dental floss comprising:
a hand grip provided with an output shaft having a longitudinal axis, said hand grip incorporating a motor and a drive mechanism powered by said motor to cause said output shaft to vibrate along said longitudinal axis;
a floss connected to said output shaft and stretched to extend in a direction substantially parallel to said longitudinal axis so as to be driven by said output shaft to vibrate in that direction;
means connected to said drive mechanism for selectively imparting said vibrating motion along said longitudinal axis and a vibrating motion about said longitudinal axis.

7. A powered dental floss as set forth in claim 6, wherein said floss extends in parallel with said longitudinal axis and is offset therefrom to a slight extent.

8. A powered dental floss comprising;
a hand grip provided with an output shaft having a longitudinal axis, said hand grip incorporating a motor and a drive mechanism powered by said motor to cause said output shaft to vibrate along said longitudinal axis;
a floss connected to said output shaft and stretched to extend in a direction substantially parallel to said longitudinal axis so as to be driven by said output shaft to vibrate in that direction;
a load detector which monitors a load being applied to said motor and provides an output signal indicative of said load being monitored; and
a controller which, in response to said output signal, varies an operational speed of said drive mechanism in order to correspondingly change the vibration rate of said output shaft.

9. A powered dental floss comprising:
a hand grip provided with an output shaft having a longitudinal axis, said hand grip incorporating a motor and a drive mechanism powered by said motor to cause said output shaft to vibrate along said longitudinal axis;
a floss connected to said output shaft and stretched to extend in a direction substantially parallel to said longitudinal axis so as to be driven by said output shaft to vibrate in that direction;
a load detector which monitors an overload condition of said motor and provide an overload signal indicative thereof; and
a controller which, in response to said overload signal, stops operating said drive mechanism.

10. A powered dental floss comprising:
a hand grip provided with an output shaft having a longitudinal axis, said hand grip incorporating a motor and a drive mechanism powered by said motor to cause said output shaft to vibrate along said longitudinal axis;
a floss connected to said output shaft and stretched to extend in a direction substantially parallel to said longitudinal axis so as to be driven by said output shaft to vibrate in that direction;
said drive mechanism including means for varying the vibration stroke of said output shaft.

11. A powered dental floss comprising:
a hand grip provided with an output shaft having a longitudinal axis, said hand grip incorporating a motor and a drive mechanism powered by said motor to cause said output shaft to vibrate along said longitudinal axis;
a floss supported on a floss attachment which is detachably connected to said output shaft and stretched to extend in a direction substantially parallel to said longitudinal axis so as to be driven by said output shaft to vibrate in that direction.

12. A powered dental floss as set forth in claim 11, wherein said floss is driven to vibrate along the longitudinal axis of said output shaft.

13. A powered dental floss as set forth in claim 11, wherein said floss attachment include a motion-converting mechanism for transforming a motion of said output shaft into a vibrating motion of said floss along a length of said floss.

14. A powered dental floss as set forth in claim 11, wherein said floss attachment is molded from a plastic material into which said floss is integrally embedded.

15. A powered dental floss as set forth in claim 11, wherein said floss is supported on a holder which is detachable to said floss attachment.

16. A powered dental floss as set forth in claim 11, wherein said attachment includes angle means of angularly displacing said floss in relation to said longitudinal axis of said output shaft.

* * * * *